(12) United States Patent
Misener et al.

(10) Patent No.: US 7,616,317 B2
(45) Date of Patent: Nov. 10, 2009

(54) REFLECTOMETER AND ASSOCIATED LIGHT SOURCE FOR USE IN A CHEMICAL ANALYZER

(75) Inventors: Garland Christian Misener, Portland, ME (US); Philip N. Harju, Bridgton, ME (US); Daniel J. Kostura, Sr., Georgetown, MA (US)

(73) Assignee: IDEXX Laboratories, Incorporated, Westbrook, ME (US)

( * ) Notice: Subject to any disclaimer, the term of this patent is extended or adjusted under 35 U.S.C. 154(b) by 139 days.

(21) Appl. No.: 11/286,079

(22) Filed: Nov. 23, 2005

(65) Prior Publication Data

US 2006/0109475 A1   May 25, 2006

Related U.S. Application Data

(60) Provisional application No. 60/630,712, filed on Nov. 24, 2004.

(51) Int. Cl.
  *G01N 33/16* (2006.01)
(52) U.S. Cl. .................. 356/446; 250/494.1; 362/249
(58) Field of Classification Search ................. 356/446; 362/554, 545, 249, 252, 362
  See application file for complete search history.

(56) References Cited

U.S. PATENT DOCUMENTS

| | | | |
|---|---|---|---|
| 3,910,701 A * | 10/1975 | Henderson et al. | 356/39 |
| 4,729,657 A | 3/1988 | Cooper et al. | 356/319 |
| 5,089,229 A | 2/1992 | Heidt et al. | 422/64 |
| 5,296,194 A * | 3/1994 | Igarashi | 422/82.05 |
| 6,661,521 B1 | 12/2003 | Stern | 356/446 |
| 6,711,516 B2 | 3/2004 | Samsoondar | 702/86 |
| 2003/0151746 A1 | 8/2003 | Sperling et al. | 356/446 |
| 2003/0189831 A1* | 10/2003 | Yoneda | 362/294 |
| 2004/0019459 A1 | 1/2004 | Dietz et al. | 702/184 |

* cited by examiner

*Primary Examiner*—Gregory J Toatley, Jr.
*Assistant Examiner*—Rebecca C Slomski
(74) *Attorney, Agent, or Firm*—Gerald T. Bodner

(57) ABSTRACT

A light source for a reflectometer which is used in a chemical analyzer includes a plurality of light emitting devices. Some of the light emitting devices emit light of different wavelengths. The light emitting devices are arcuately arranged about a circle having a predetermined radius. Adjacent light emitting devices are spaced from each other a predetermined distance. The light emitting devices are positioned to direct light emitted therefrom to an illumination plane. At least two, but preferably three or four, of the light emitting devices emit light of substantially the same wavelength and are illuminated simultaneously to provide a volume of substantially homogenous irradiance at the illumination plane.

14 Claims, 20 Drawing Sheets

REFLECTOMETER AND ASSOCIATED LIGHT SOURCE FOR USE IN A CHEMICAL ANALYZER

CROSS-REFERENCE TO RELATED APPLICATION

This application is related to U.S. provisional application Ser. No. 60/630,712, filed on Nov. 24, 2004, and entitled "Reflectometer With Minimal Sensitivities To Object Position And Inhomogeneities", the disclosure of which is incorporated herein by reference. This application claims the benefit of priority under 35 U.S.C. §119 to the aforementioned related provisional application.

BACKGROUND OF THE INVENTION

1. Field of the Invention

The present invention relates to light sources for optical instruments, and more specifically relates to a light source and a reflectometer employing such a light source for use in a chemical analyzer.

2. Description of the Prior Art

There are many chemical analyzers currently being utilized for automated testing of essentially dry, analytical elements in the form of test slides. The test slides are formed as a multi-layer element containing the necessary reagents for reaction with components of a biological fluid, such as blood serum, deposited thereon. Certain reactions calorimetrically produce a change in optical density which is sensed by a reflectometer of the chemical analyzer, the amount of light reflected from the element varying in accordance with the reaction and being indicative of the amount of a particular component present in the fluid.

One such chemical analyzer having a reflectometer is disclosed in U.S. Pat. No. 5,089,229, entitled "Chemical Analyzer", which issued on Feb. 18, 1992 to Thomas Heidt, et al., the disclosure of which is incorporated herein by reference. FIGS. 18, 31a, 31b and 31c of the aforementioned Heidt et al. patent illustrate the reflectometer assembly of the analyzer disclosed therein. The reflectometer assembly includes several light sources, including fluorescent lamps or tubes and light emitting diodes (LEDs), each of the light sources emitting a light of different wavelength.

FIG. 1 of the present application corresponds to FIG. 31b of the aforementioned Heidt et al. patent, and illustrates the LED light source assembly 426 disclosed in the Heidt et al. patent. The LED light source assembly basically includes a mounting block 458 situated below a rotatable turntable 50 which carries reagent test slides. The mounting block 458 includes a plurality of spaced apart bores 460 formed through its thickness. Each bore is sloped to the vertical and, preferably, is at an angle of 45 degrees to the vertical. In a preferred form of the invention, four bores 460 are formed spaced equally distantly about the general periphery of the mounting block 458.

Four light emitting diodes (LEDs) 462, each emitting a light of different wavelength, are mounted in the underside of the mounting block 458, each LED 462 being received by a corresponding bore 460. The mounting block 458 is situated with respect to the rotatable turntable 50 such that light emitted by any one of the LEDs will impinge on the bottom of the film portion 124 of a test slide 71 carried by the rotatable turntable 50.

A bore 464 is formed centrally through the mounting block 458. A collimating lens 466 is mounted in the bore 464 and near the top surface of the block 458. A photodiode 468 is also mounted in the bore 464 and near the lower surface of the block 458. Interposed between the lens 466 and the photodiode 468 and in bore 464 is an infrared rejection filter 470.

Light from any LED 462 impinging on the test slide 71 will be reflected directly into the photodiode 468 through the lens 466 and filter 470. The photodiode will provide a signal indicative of the amount of light reflected to the associated circuitry of the reflectometer.

As described in the aforementioned Heidt et al. patent, four LEDs 462 are provided, each LED emitting a light of different wavelength. The preferred wavelengths emitted by the LEDs are in the following ranges: about 555 to about 565 nm; about 585 to about 595 nm; about 635 to about 645 nm; and about 675 to about 685 nm. The aforementioned Heidt et al. patent states that the optimal wavelength for each of the LEDs is 560 nm, 590 nm, 640 nm and 680 nm, respectively. Preferably, the latter two LEDs (i.e., 640 nm and 680 nm LEDs) are disclosed in the aforementioned Heidt et al. patent as having associated therewith filters 469 of the desired wavelength (i.e., 640 and 680 nm) positioned in their respective bores 460.

The aforementioned Heidt et al. patent describes each of the four LEDs 462 as being individually energized so that a single beam of light having a particular wavelength or range of wavelengths will be selected to impinge on a particular test slide.

Various tests to be performed by the chemical analyzer require different test slides, where each test slide carries a different dry analyte. The various test slides must be exposed to light of selected frequencies in order to conduct a reflectometry test. The type of test slide, for example, for a calcium test, is provided by bar code information carried on the test slide, which bar code information is read by a bar code optical scanner of the chemical analyzer and which is provided to the associated computer and circuitry of the analyzer. The computer of the analyzer will energize an appropriate light source, that is, either one of the fluorescent tubes or one of the LEDs, during the analysis operation when a particular test slide 71 is situated in alignment with a particular light source. For a detailed description of how the chemical analyzer uses reflective light to determine the concentration of the chemistry in the serum deposited on the test slide, reference should be had to the aforementioned Heidt et al. patent.

The chemical analyzer with the reflectometer described above of the aforementioned Heidt et al. patent has been successfully commercialized for many years and provides accurate test results. The present invention is directed to an improvement in the reflectometer disclosed in the aforementioned Heidt et al. patent.

OBJECTS AND SUMMARY OF THE INVENTION

It is an object of the present invention to provide a light source for use in a reflectometer of a chemical analyzer.

It is another object of the present invention to provide a light source which generates a volume of substantially homogeneous light.

It is yet another object of the present invention to provide a light source for a reflectometer in a chemical analyzer that generates an evenly distributed density of light at a plane.

It is a further object of the present invention to provide a reflectometer employing a light source for use in a chemical analyzer.

It is yet a further object of the present invention to provide a reflectometer employing a light source for use in a chemical analyzer that overcomes the inherent disadvantages of conventional reflectometers.

It is still another object of the present invention to provide a method of illuminating an object at a plane and generating thereat a volume of substantially homogeneous light irradiance at any point within the volume.

In accordance with one form of the present invention, a light source for a reflectometer for use with a chemical analyzer includes a plurality of light emitting devices, such as light emitting diodes, at least some of which emit light of different wavelengths. The light emitting devices are arcuately arranged about a circle having a predetermined diameter for those sources with substantially the same wavelengths and viewing angles. Sources emitting light of substantially different viewing angles need not be arranged at the same diameter. The light emitting devices are positioned to direct light emitted therefrom on a plane. Adjacent light emitting devices are spaced from each other a predetermined distance. At least two of the light emitting devices emit light of the same wavelength and are illuminated simultaneously to provide a volume of substantially homogenous light irradiance at the plane.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

In accordance with one form of the present invention, a plurality of light emitting devices is arranged in a circle or partial circle having a predetermined diameter. The light emitting devices, which are preferably light emitting diodes (hereinafter LEDs), each having a semiconductor die, are positioned to direct the light emitted from the LEDs onto a reagent test slide. At least two, and preferably three or four, of the LEDs emit light of the same wavelength. As desired, other LEDs that emit light of different wavelengths are also included. The LEDs of the same wavelength are illuminated simultaneously to provide a volume of substantially homogeneous light irradiance at the plane in which the reagent test slide resides.

While the examples presented in the description of this invention are generally relevant to a circular or semi-circular arrangement of LEDs, it will be noted throughout that the methods for optimizing placement and calibration of the sources also apply to arrangements with substantially rectangular and other (including no) symmetries. The rectangular case will be more effective for substantially homogeneous illumination of rectangular objects. In general, the geometry of the object to be illuminated influences the optimal arrangement of its illumination sources.

Figure 1:
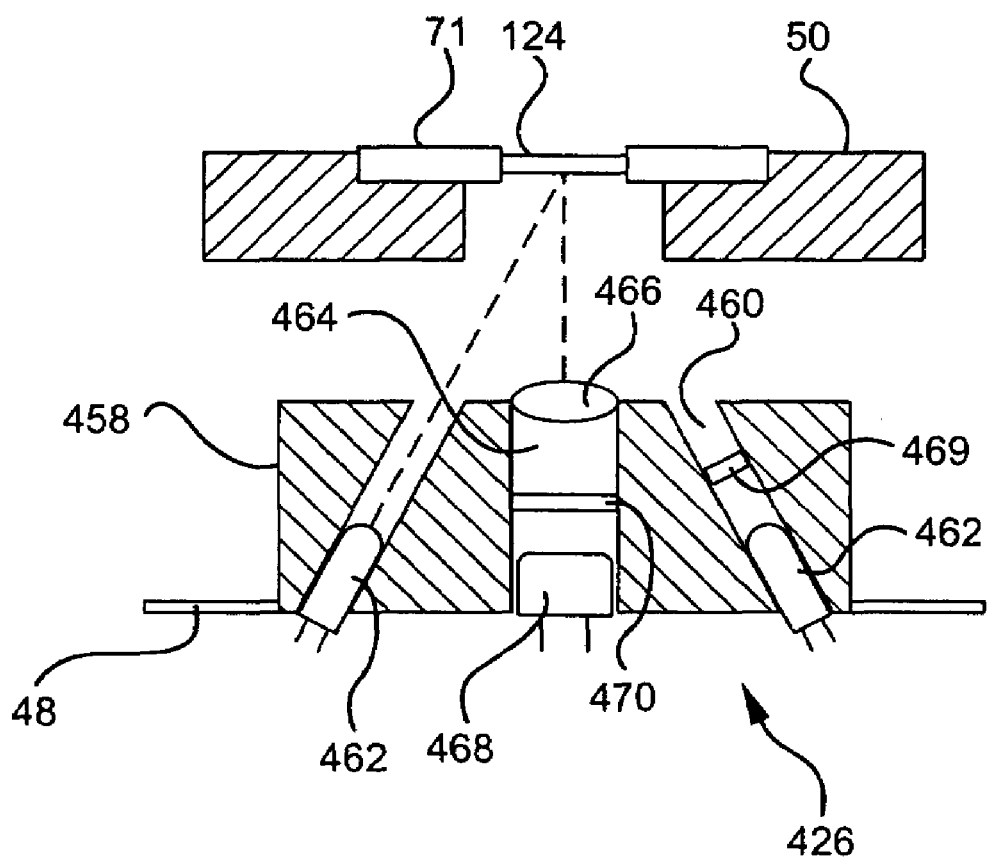
FIG. 1 is a cross-sectional view of a conventional light source and reflectometer used in a currently marketed chemical analyzer.
Figure 2:
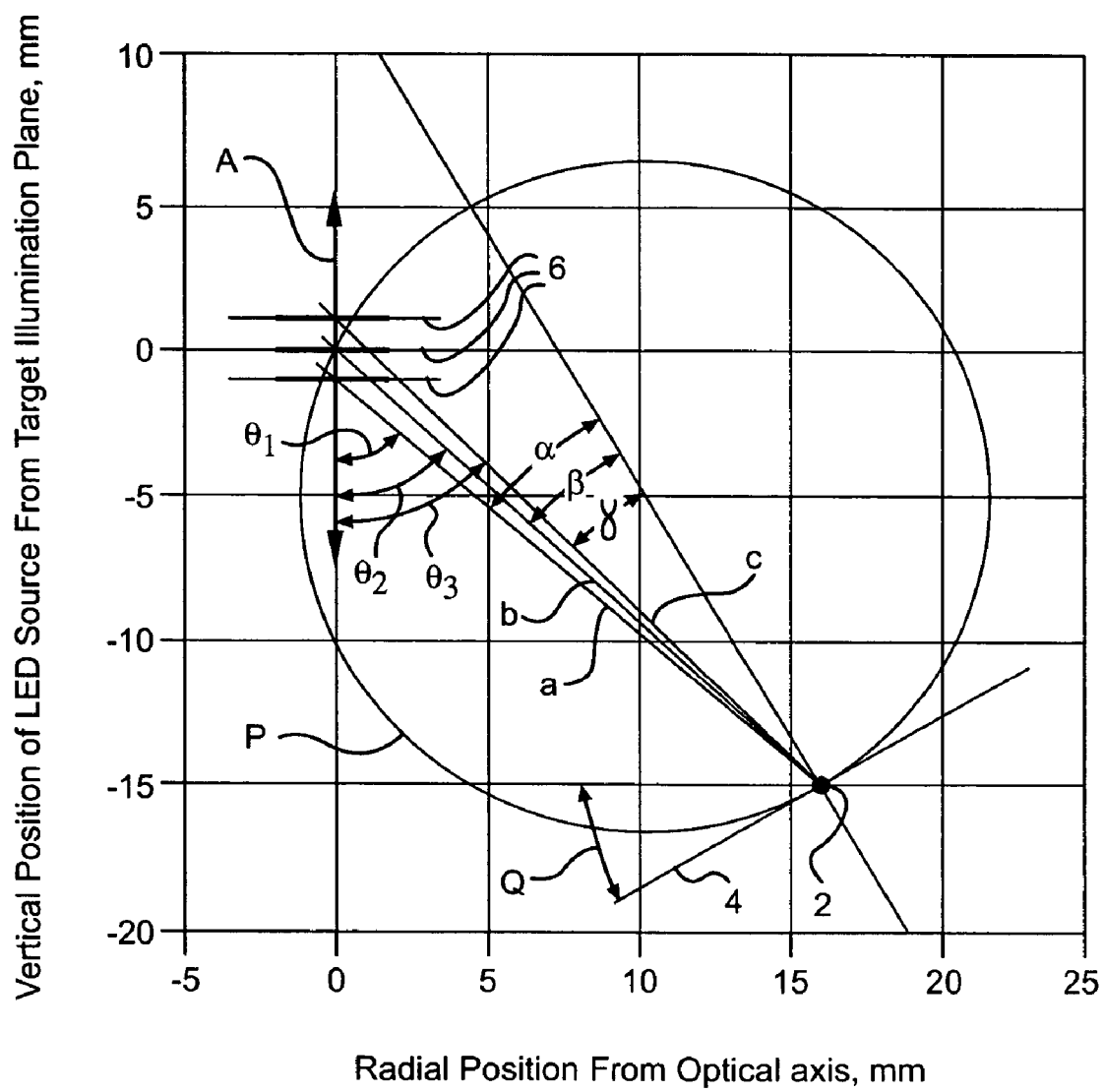
FIG. 2 is a schematized cross-section of the relative light flux emitted by a conventional 120 degree (wide) viewing angle LED, and the balancing of the irradiance on an illumination plane, in order to make the irradiance relatively insensitive to small changes in the vertical position of the illumination plane.

FIG. 2 shows a schematized cross-section of the relative light flux emitted by a 120 degree (wide) viewing angle LED 2. The LED die is assumed to be located at the center of the angled board 4 at the lower right-hand side of FIG. 2 when viewing the figure. The LED emission profile, denoted in FIG. 2 by circle P, which is the relative intensity at a given angle, is proportional to the length of the chord (e.g., a, b, c) from the LED mounting position at a particular LED emission angle (e.g., $\alpha$, $\beta$, $\gamma$, respectively). The angles of incidence the light makes with the optical axis, A, are denoted in FIG. 2 by the symbols $\theta_1$, $\theta_2$ and $\theta_3$. The active region of the slide 6 is denoted in FIG. 2 by a thin line, and the detection region of the slide 6 is denoted by a thick line. The active region refers to the viewing window of the slide, where the "chemistry chip" is exposed. Outside of this area is the slide frame. The detection region of the slide is that part of the viewing window that the detection optics is able to "see" within its field of view. The test slide 6 is shown in FIG. 2 at the desired location (i.e., the center position, at 0 on the vertical scale in FIG. 2), and at the 1 millimeter (mm) higher and 1 mm lower positions from the center position. The LED mounting angle is denoted in FIG. 2 by the letter Q.

The most light intensity is emitted normal to the die, and drops to zero at ±90 degrees to the die normal. At ±60 degrees to the normal, the intensity has dropped to one half of the intensity at 0 degrees; by definition, this means that the LED depicted has a 120 degree viewing angle. A reagent test slide 6 is depicted at (x, y)=(0, 0) in FIG. 2, and the center ray from the LED 2 is shown striking the center of the slide 6. If, for reason of mounting imprecision or inaccuracy, or any other reason, the slide 6 moves upward to (x, y)=(0, 1), for example, as shown in FIG. 2, then the irradiance at the center of the slide would decrease if the LED's intensity were equal in all directions, due to the fact that the distance from the source to the target has increased. The proportional decrease in intensity would be $r_i^2/r_f^2$, where $r_i$ is the initial source-to-target distance, and $r_f$ is the corresponding final distance. However, by judicious choice of the LED mounting position and angle, and the LED viewing angle, one can substantially match the irradiance loss at the slide 6 due to increased distance with an irradiance gain resulting from the smaller LED emission and slide incidence angles. Similarly, moving the slide 6 downward to (x, y)=(0, −1), for example, decreases the source-to-target distance but increases the LED emission and slide incidence angles. Again, by carefully choosing the LED viewing angle, and mounting position and angle, the effects of vertical placement on slide irradiance can be substantially balanced.

The reason the incidence angle can be important for creating a volume of substantially consistent irradiance is because what is often really desired is substantially consistent irradiance as detected by an optical sensor, imaging device or machine vision system. In this very common case, it is desirable to match the irradiance characteristics to the detector's positional sensitivity to reflected and/or emitted light intensity. For light diffusely reflected from a so-called Lambertian surface, the reflected intensity will be proportional to the cosine of the angle of incidence of the illuminating light. For specularly-reflected light, the relation between the angle of a reflected ray from the object to the detection system and the angle of incidence (source to object) is important. For capturing light by a lens, a general approximation is that the sensitivity to light drops off proportional to the fourth power of the cosine of the angle of incidence on the entrance pupil of the lens. In this invention, when applied to a source for reflectometry, front surface fluorometry, microscopy, or densitometry, "substantially consistent irradiance" is interpreted to mean that the effects of the irradiance on a planar surface, as detected by the desired detection system, are substantially consistent regardless of its placement within a defined volume, as long as the surface is placed substantially perpendicularly to the system or composite optical axis.

Also, by spacing multiple LEDs 2 configured as depicted in FIGS. 5, 6A, 6B, 7A and 7B symmetrically around the slide 6, a circular area of substantially constant irradiance can be developed on a slide. Two LEDs mounted on opposite sides of the reading slide will substantially flatten (i.e., make consistent) the illumination field, but significantly better performance is achieved with three LEDs mounted at 120 degree intervals around the slide. Four LEDs mounted at 90 degree intervals improves flat fielding still further, but advantages diminish for incorporating even more wide viewing angle LEDs when source-to-object distances are relatively small, such as on the order described in FIGS. 3C-3N. Three or at most four LEDs 2 are preferred for achieving a flat illumination field, unless more LEDs are needed for adequate irradiance.

The combination of symmetric spacing of LEDs 2 about the object to be illuminated, and the mounting and viewing angle selections of these LEDs can be combined to provide a volume of substantially consistent irradiance anywhere within that volume, given that no obstructions are placed before the point to be irradiated. A significant portion of this invention is the disclosure of this method of providing at least one set of LEDs 2 that provide a substantially homogeneous irradiance within a defined approximately spherical volume 8, for use as a light source for reflectometry, front surface fluorometry, microscopy, and densitometry. However, if the object to be illuminated is not circular, this invention still applies. In other cases, for example, optimal arrangement of LEDs emitting the same wavelength band may be as two or more spaced-apart rows, the rows often being angled relative to one another and to the object to be illuminated. In these cases, the volume of substantially homogeneous irradiance will be generally ellipsoidal in shape.

Figure 3A:
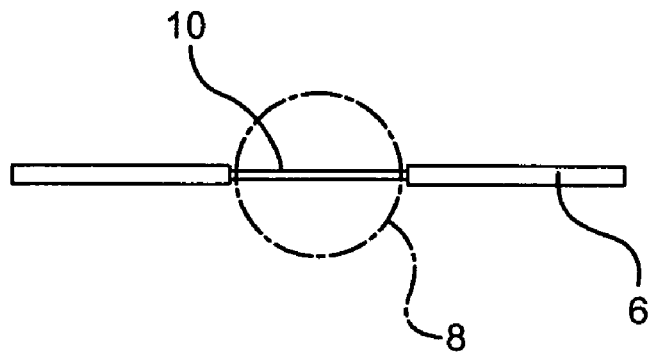
FIG. 3A is a cross-sectional view of a chemical reagent test slide and a superimposed volume of substantially homogeneous light irradiance generated by the light source of the present invention.
Figure 3B:
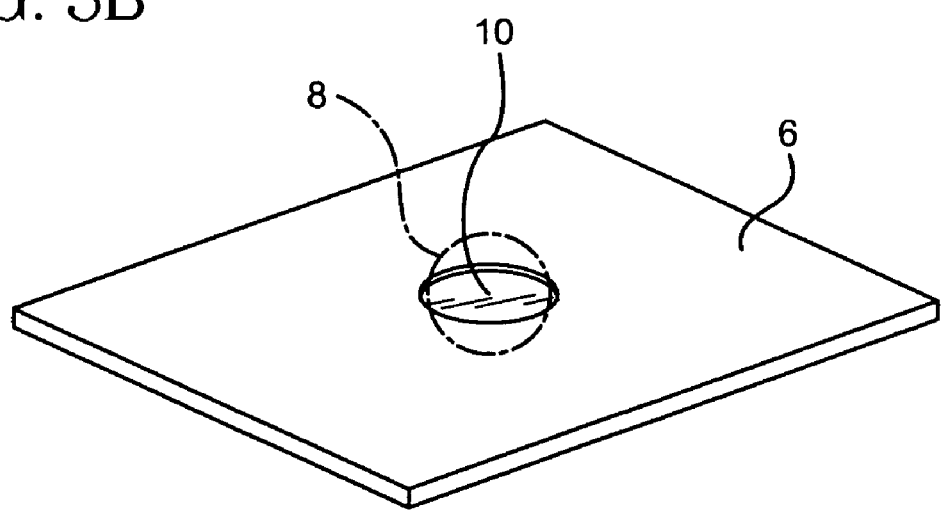
FIG. 3B is a perspective view of a chemical reagent test slide and the same superimposed volume of substantially homogeneous light irradiance encompassing a portion of the test slide and provided by the light source of the present invention.

This volume 8 of substantially homogeneous light irradiance is illustrated by the cross-sectional view of a reagent test slide 6 shown in FIG. 3A and the perspective view of the slide shown in FIG. 3B of the drawings. By having at least two LEDs 2 emit light of the same wavelength simultaneously and directing this light at the plane where the reagent test slide is situated, the film portion 10 of the reagent test slide 6 will fall within the volume 8 of substantially homogeneous light irradiance. Thus, even if the reagent test slide is slightly misaligned with respect to the desired optical plane in either the (x, y) plane or the z-axis, the film portion 10 will still be within this volume of substantially consistent irradiance which is created by the light source of the present invention. This design will provide more accurate readings based on the light reflected from the film portion 10 and received by the optical sensor of the reflectometer. Accordingly, the present invention provides an inexpensive method of minimizing, in particular, the z-axis variability in the positioning of the test slides 6, as well as (x, y) plane variability.

Figure 3C:
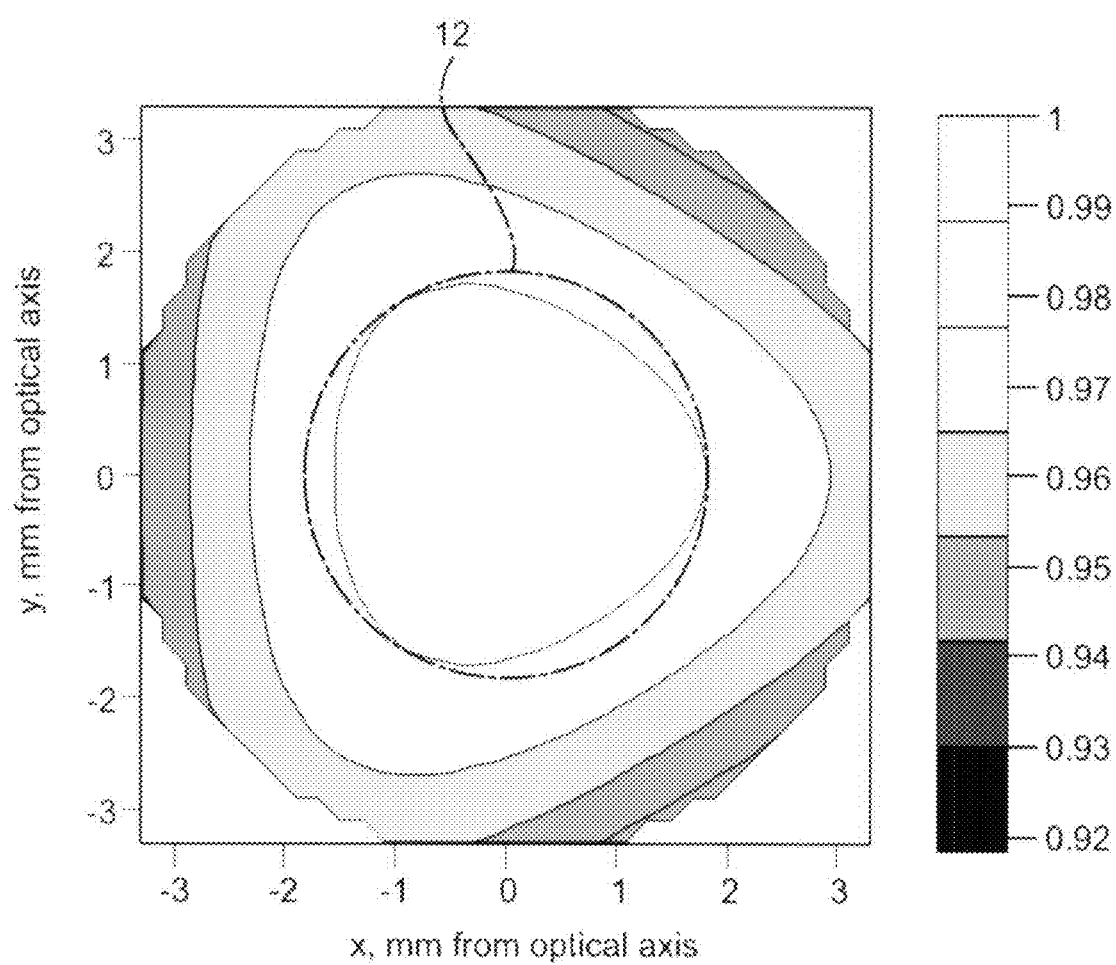
FIG. 3C is a photograph of a filled contour schematic of the light irradiance available at (x,y) positions relative to the system or composite optical axis of three equally spaced LEDs of the same wavelength and at a vertical position judged optimal for minimizing the z-axis sensitivity of the irradiance to the vertical position of the slide shown in FIGS. 3A and 3B. The scale indicates the percentage of light available at different positions, relative to the maximum irradiance within the volume depicted in FIG. 3D. The irradiance contour schematic of FIG. 3C is denoted in FIG. 3D by the reference letter C. The irradiance contour depicted by FIG. 3C is situated in an (x,y) plane at a height of 14.83 mm (millimeters) above the plane in which the bases of the three LEDs reside.

FIG. 3C plots the irradiance contours at (x,y) positions relative to the system optical axis and at a vertical position judged optimal for minimizing the z-axis sensitivity of the irradiance to the vertical position of the slide shown in FIGS. 3A and 3B, in one embodiment of the present invention. The jagged edges in this and similar figures are an artifact of dividing a circular object area into square incremental areas for modeling the irradiance at regularly-spaced locations within the object. The added dashed-line circle 12 shows the limits of detectable reflected light intensity in this example. Note the three-fold symmetry of the irradiance contours, resulting from three LEDs each mounted at 120 degrees relative to the other two, beginning at a 0 degree angle relative to the x-axis.

Figure 3D:
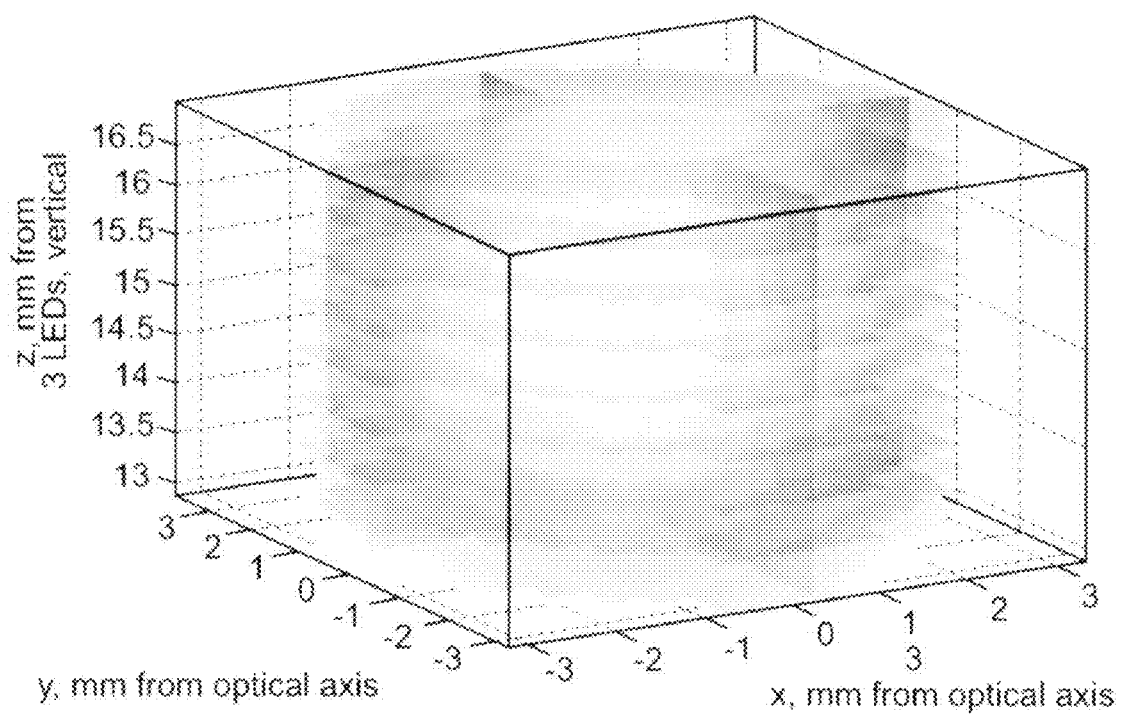
FIG. 3D is a photograph of a three dimensional graph depicting nine horizontal and two vertical planes of illumination irradiance, using the same grayscale scheme as FIG. 3C, but with the darker shades of gray made partially transparent to aid 3D visualization of the volume of substantially homogeneous light irradiance.
Figure 3E:
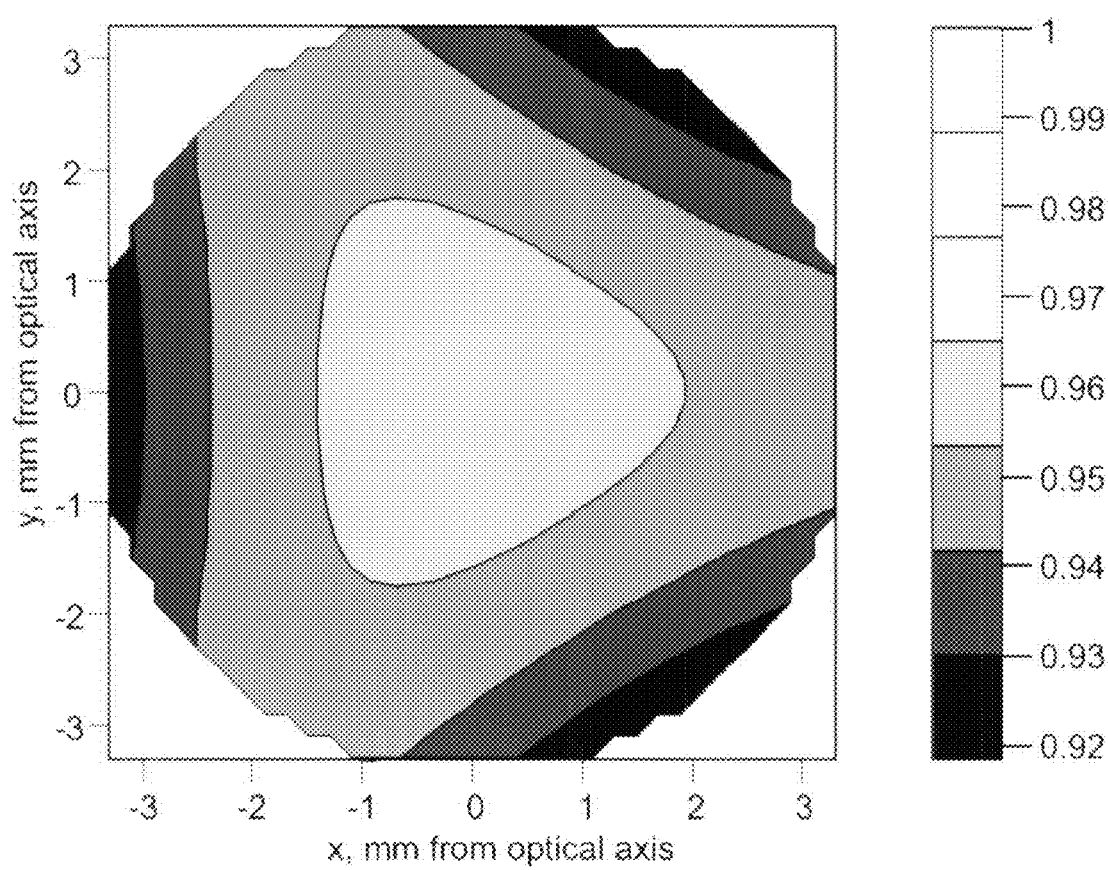
FIG. 3E is a photograph of a filled contour schematic of the light irradiance available at (x,y) positions relative to the system or composite optical axis of three equally spaced LEDs of the same wavelength and at a vertical position relative to the plane in which the bases of the three LEDs reside. The scale indicates the percentage of light available at different positions, relative to the maximum irradiance within the volume depicted in FIG. 3D. The irradiance contour depicted by FIG. 3E is situated in a horizontal (x,y) plane at a height of 12.83 mm above the plane in which the bases of the three LEDs reside.
Figure 3F:
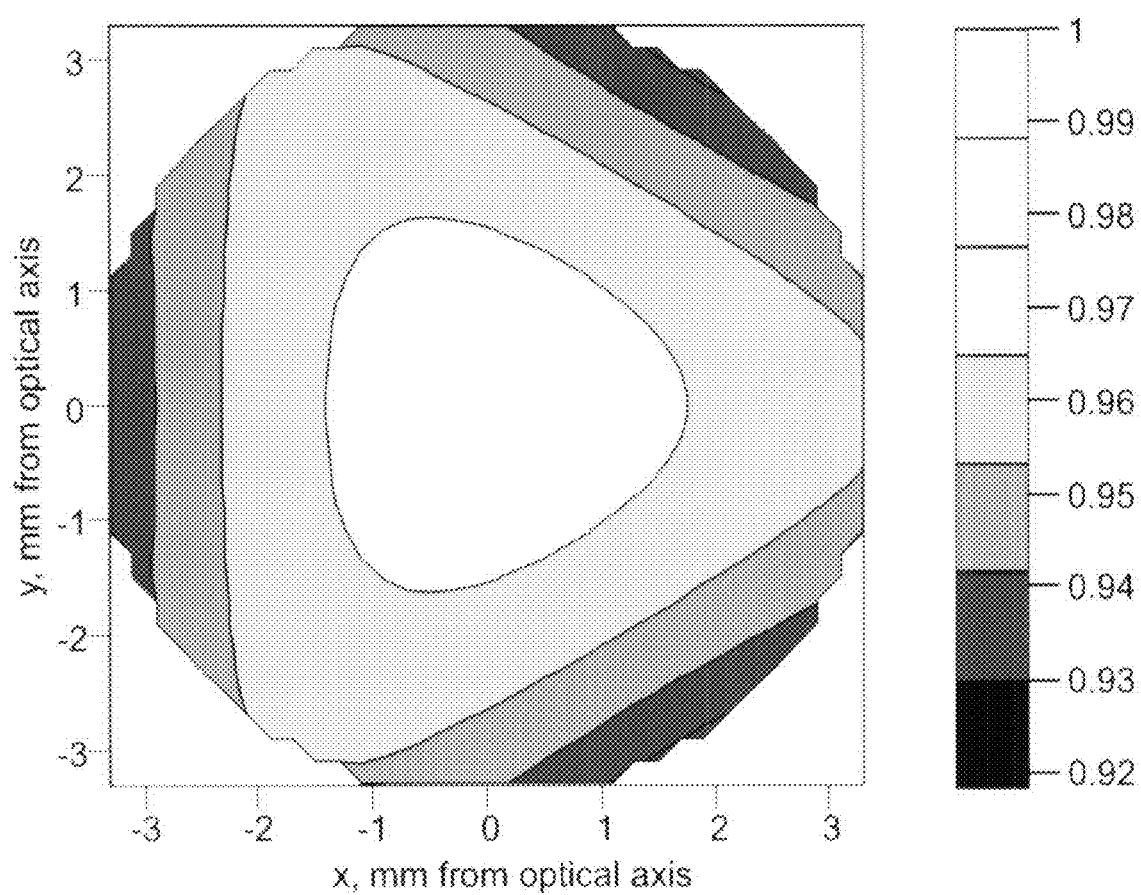
FIG. 3F is a photograph of a filled contour schematic of the light irradiance available at (x,y) positions relative to the system or composite optical axis of three equally spaced LEDs of the same wavelength and at a vertical position relative to the plane in which the bases of the three LEDs reside. The scale indicates the percentage of light available at different positions, relative to the maximum irradiance within the volume depicted in FIG. 3D. The irradiance contour depicted by FIG. 3F is situated in a horizontal (x,y) plane at a height of 13.33 mm above the plane in which the bases of the three LEDs reside.
Figure 3G:
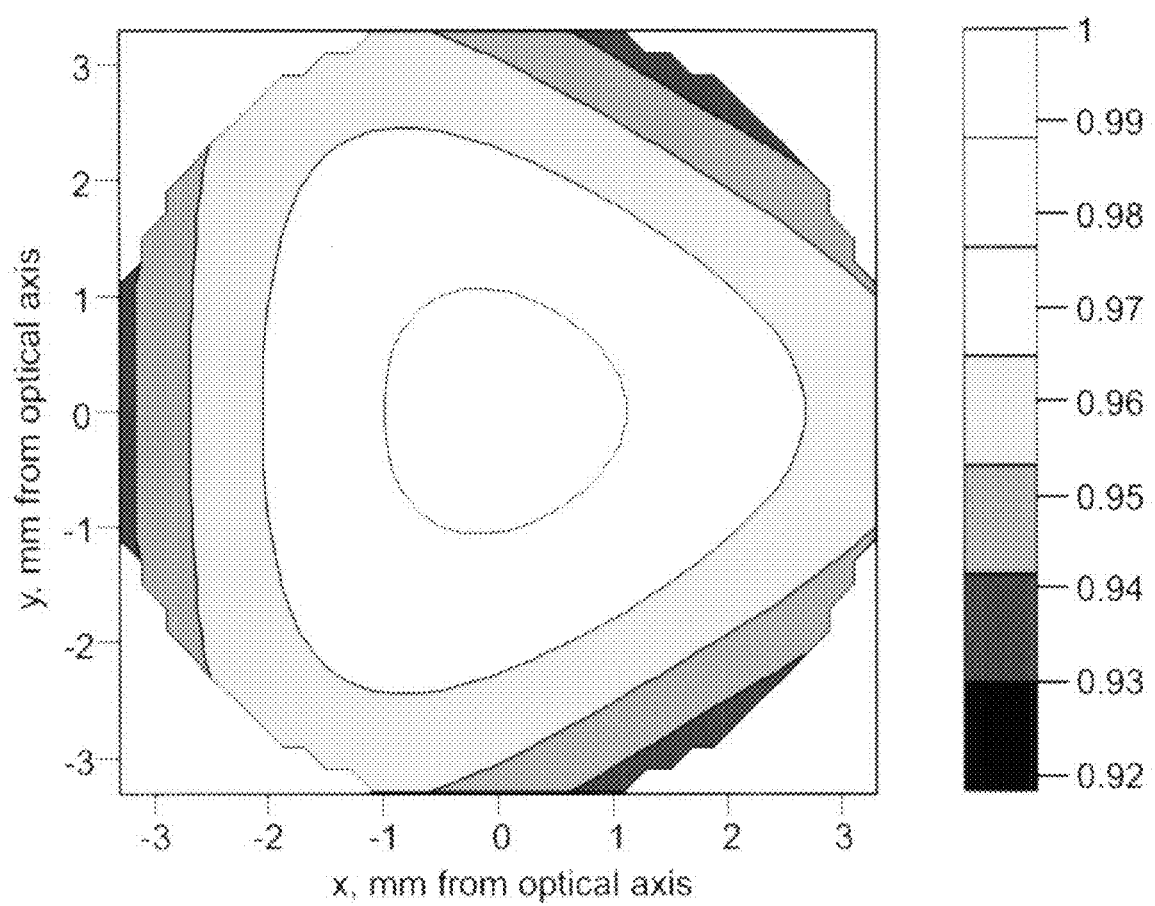
FIG. 3G is a photograph of a filled contour schematic of the light irradiance available at (x,y) positions relative to the system or composite optical axis of three equally spaced LEDs of the same wavelength and at a vertical position relative to the plane in which the bases of the three LEDs reside. The scale indicates the percentage of light available at different positions, relative to the maximum irradiance within the volume depicted in FIG. 3D. The irradiance contour depicted by FIG. 3G is situated in a horizontal (x,y) plane at a height of 13.83 mm above the plane in which the bases of the three LEDs reside.
Figure 3H:
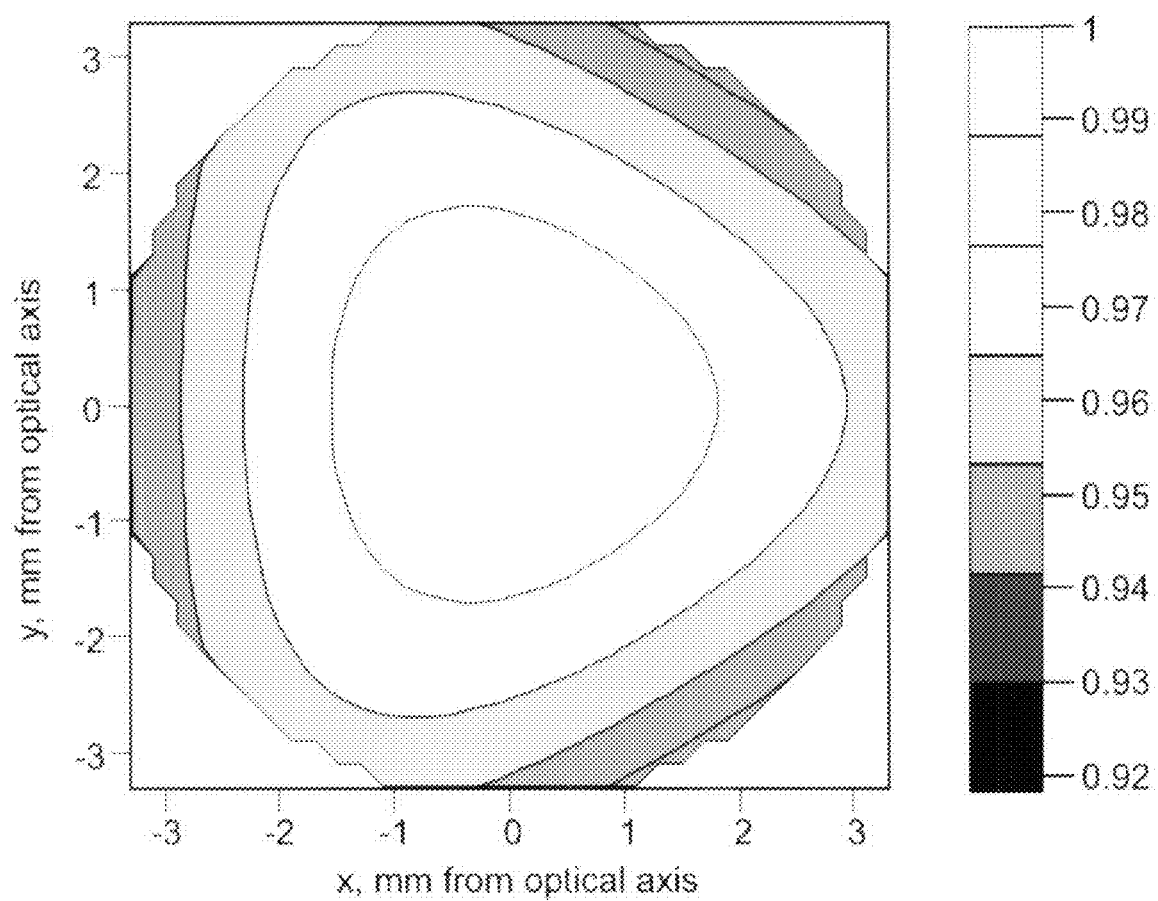
FIG. 3H is a photograph of a filled contour schematic of the light irradiance available at (x,y) positions relative to the system or composite optical axis of three equally spaced LEDs of the same wavelength and at a vertical position relative to the plane in which the bases of the three LEDs reside. The scale indicates the percentage of light available at different positions, relative to the maximum irradiance within the volume depicted in FIG. 3D. The irradiance contour depicted by FIG. 3H is situated in a horizontal (x,y) plane at a height of 14.33 mm above the plane in which the bases of the three LEDs reside.
Figure 3I:
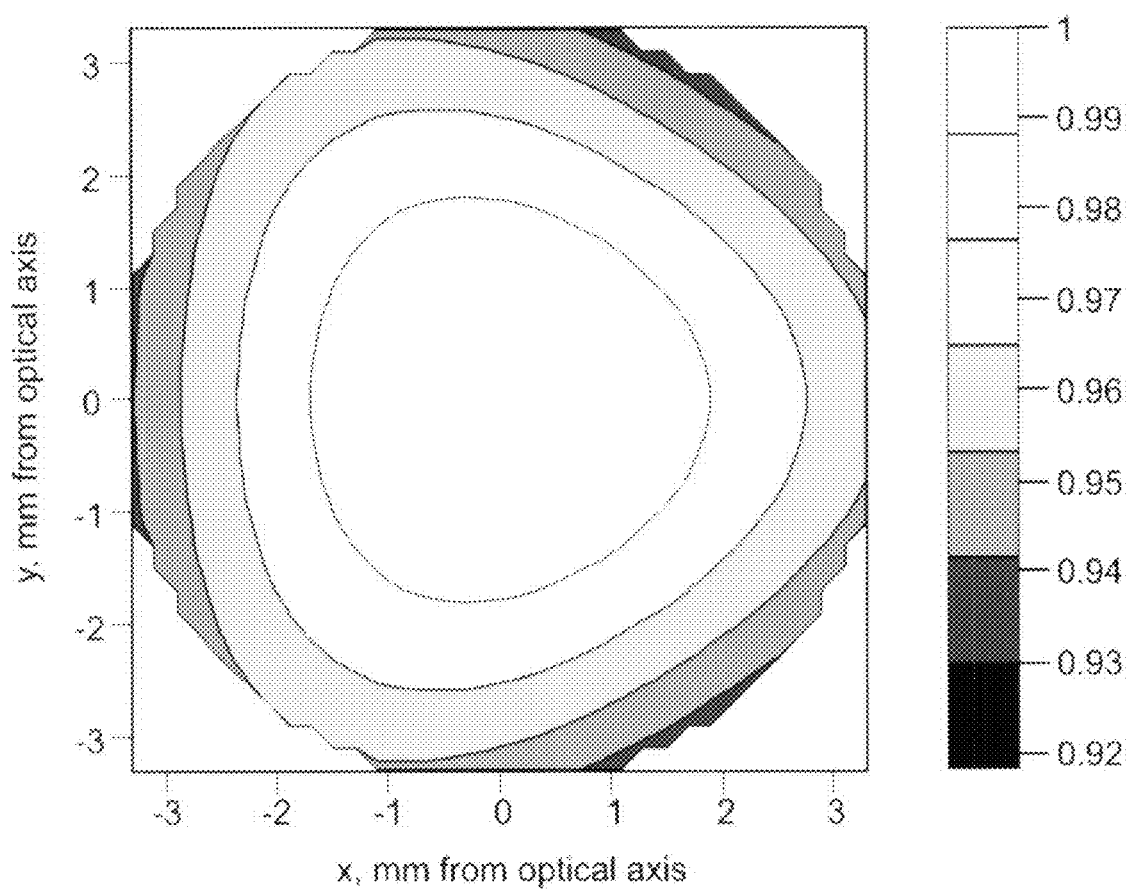
FIG. 3I is a photograph of a filled contour schematic of the light irradiance available at (x,y) positions relative to the system or composite optical axis of three equally spaced LEDs of the same wavelength and at a vertical position relative to the plane in which the bases of the three LEDs reside. The scale indicates the percentage of light available at different positions, relative to the maximum irradiance within the volume depicted in FIG. 3D. The irradiance contour depicted by FIG. 3I is situated in a horizontal (x,y) plane at a height of 15.33 mm above the plane in which the bases of the three LEDs reside.
Figure 3J:
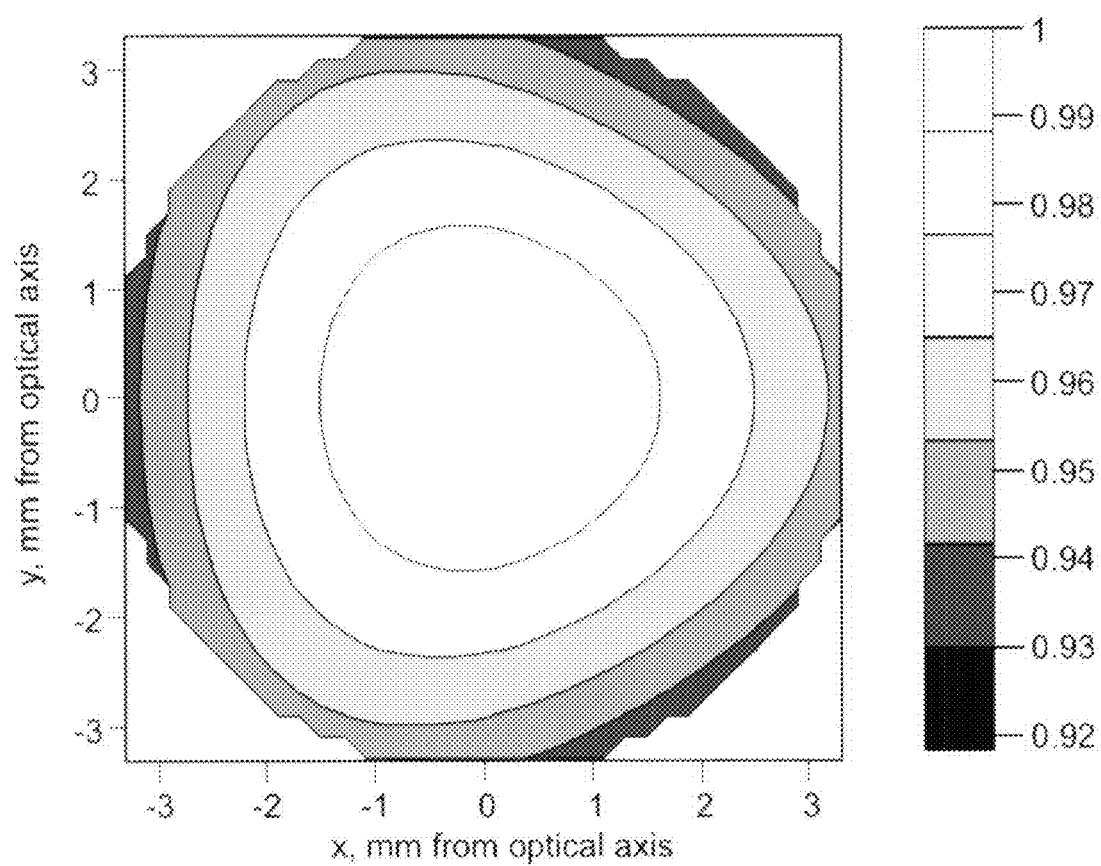
FIG. 3J is a photograph of a filled contour schematic of the light irradiance available at (x,y) positions relative to the system or composite optical axis of three equally spaced LEDs of the same wavelength and at a vertical position relative to the plane in which the bases of the three LEDs reside. The scale indicates the percentage of light available at different positions, relative to the maximum irradiance within the volume depicted in FIG. 3D. The irradiance contour depicted by FIG. 3J is situated in a horizontal (x,y) plane at a height of 15.83 mm above the plane in which the bases of the three LEDs reside.
Figure 3K:
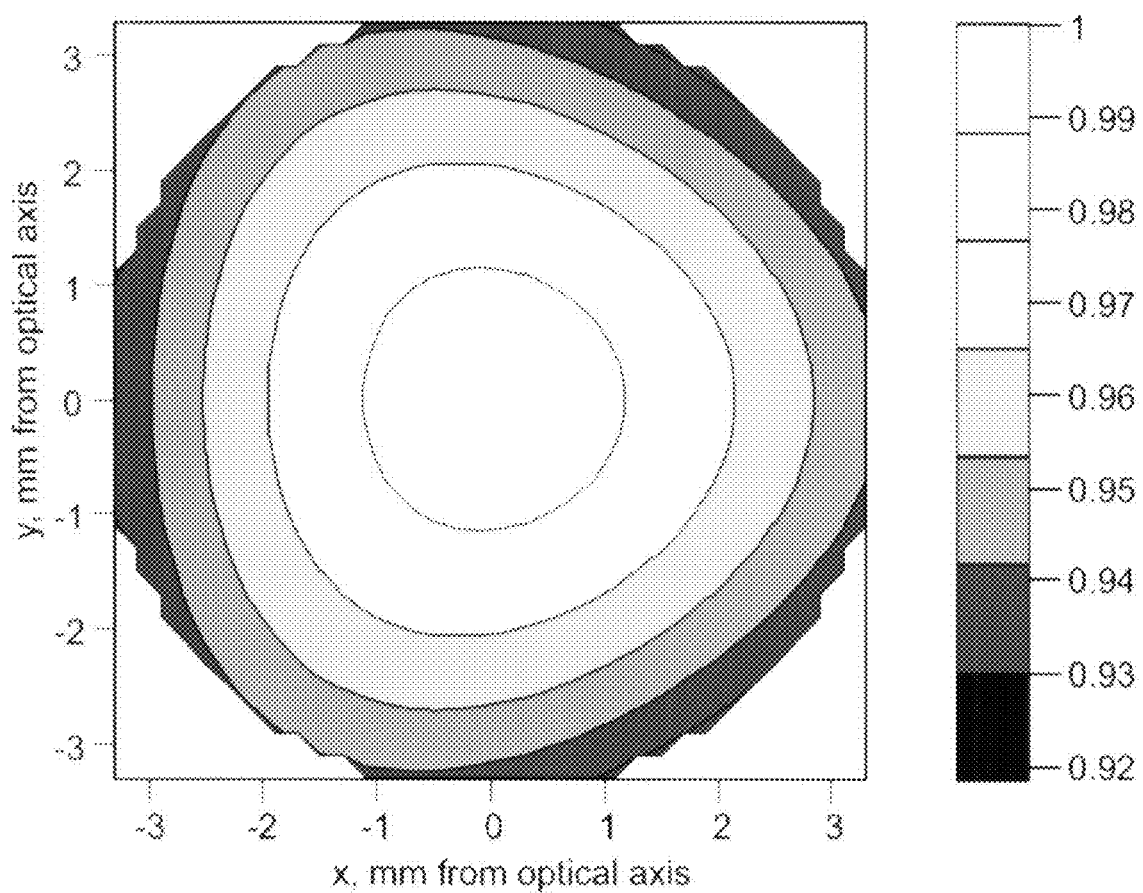
FIG. 3K is a photograph of a filled contour schematic of the light irradiance available at (x,y) positions relative to the system or composite optical axis of three equally spaced LEDs of the same wavelength and at a vertical position relative to the plane in which the bases of the three LEDs reside. The scale indicates the percentage of light available at different positions, relative to the maximum irradiance within the volume depicted in FIG. 3D. The irradiance contour depicted by FIG. 3K is situated in a horizontal (x,y) plane at a height of 16.33 mm above the plane in which the bases of the three LEDs reside.
Figure 3L:
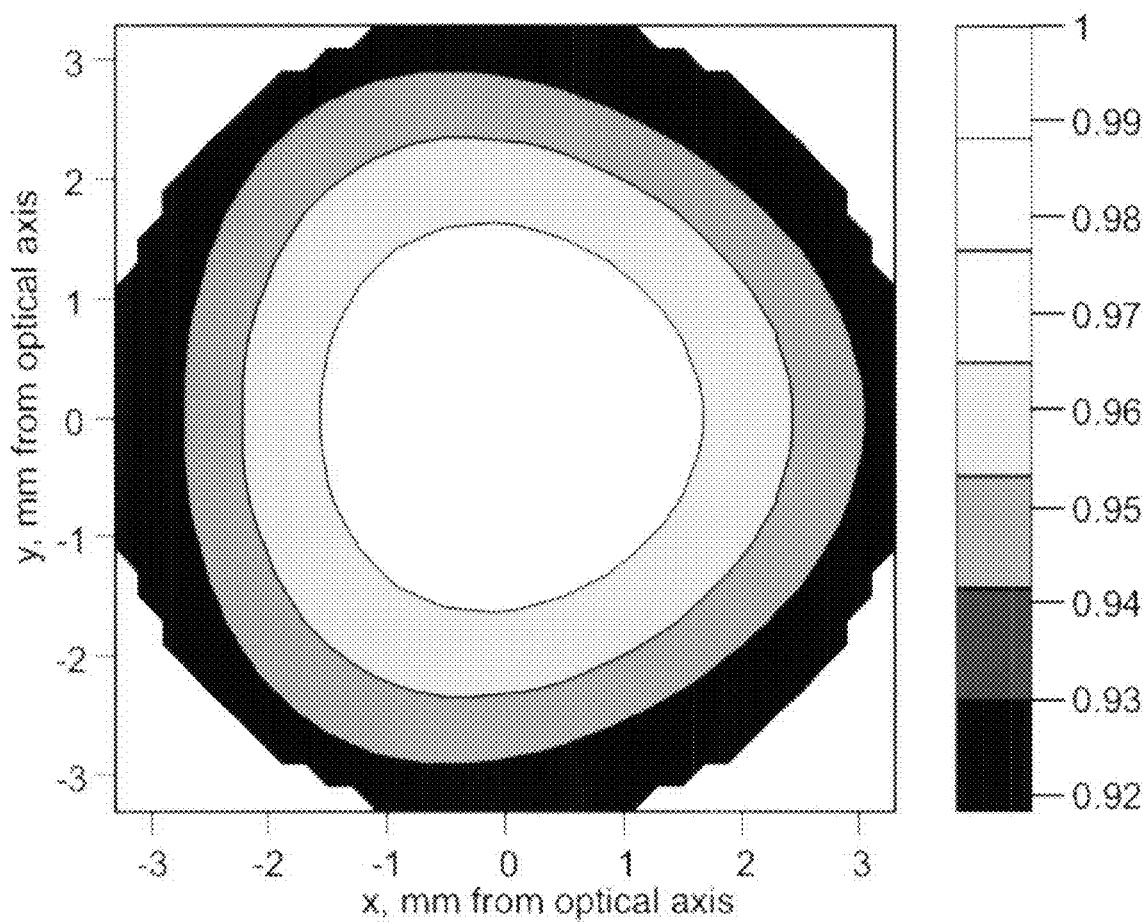
FIG. 3L is a photograph of a filled contour schematic of the light irradiance available at (x,y) positions relative to the system or composite optical axis of three equally spaced LEDs of the same wavelength and at a vertical position relative to the plane in which the bases of the three LEDs reside. The scale indicates the percentage of light available at different positions, relative to the maximum irradiance within the volume depicted in FIG. 3D. The irradiance contour depicted by FIG. 3L is situated in a horizontal (x,y) plane at a height of 16.83 mm above the plane in which the bases of the three LEDs reside.

In FIG. 3D, the planar irradiance contour shown in FIG. 3C is located at the center of the stack of nine irradiance contours spaced at 0.5 mm increments. The planes and contour shading aid in visualizing the volume of substantially homogeneous light irradiance.

Figure 3M:
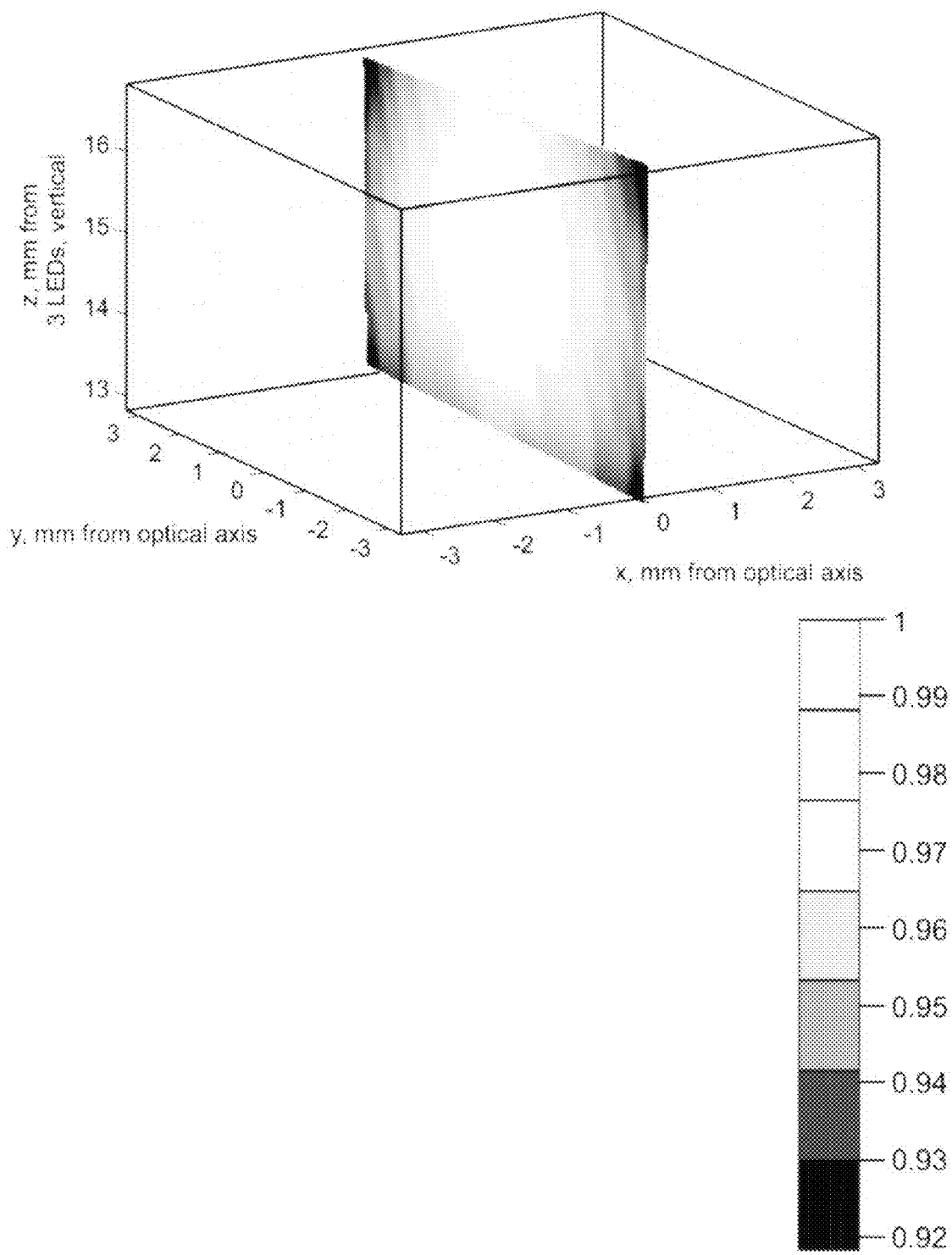
FIG. 3M is a photograph of a filled contour schematic of the light irradiance available at (x,z) positions relative to the optical system of three equally spaced LEDs of the same wavelength and shown in its relative position with respect to the three-dimensional graph of FIG. 3D. The scale indicates the percentage of light available at different positions, relative to the maximum irradiance within the volume depicted in FIG. 3D. The irradiance contour depicted by FIG. 3M is situated in a vertical (x,z) plane at a position of y=−0.1 mm from the system optical axis of the three equally spaced LEDs.
Figure 3N:
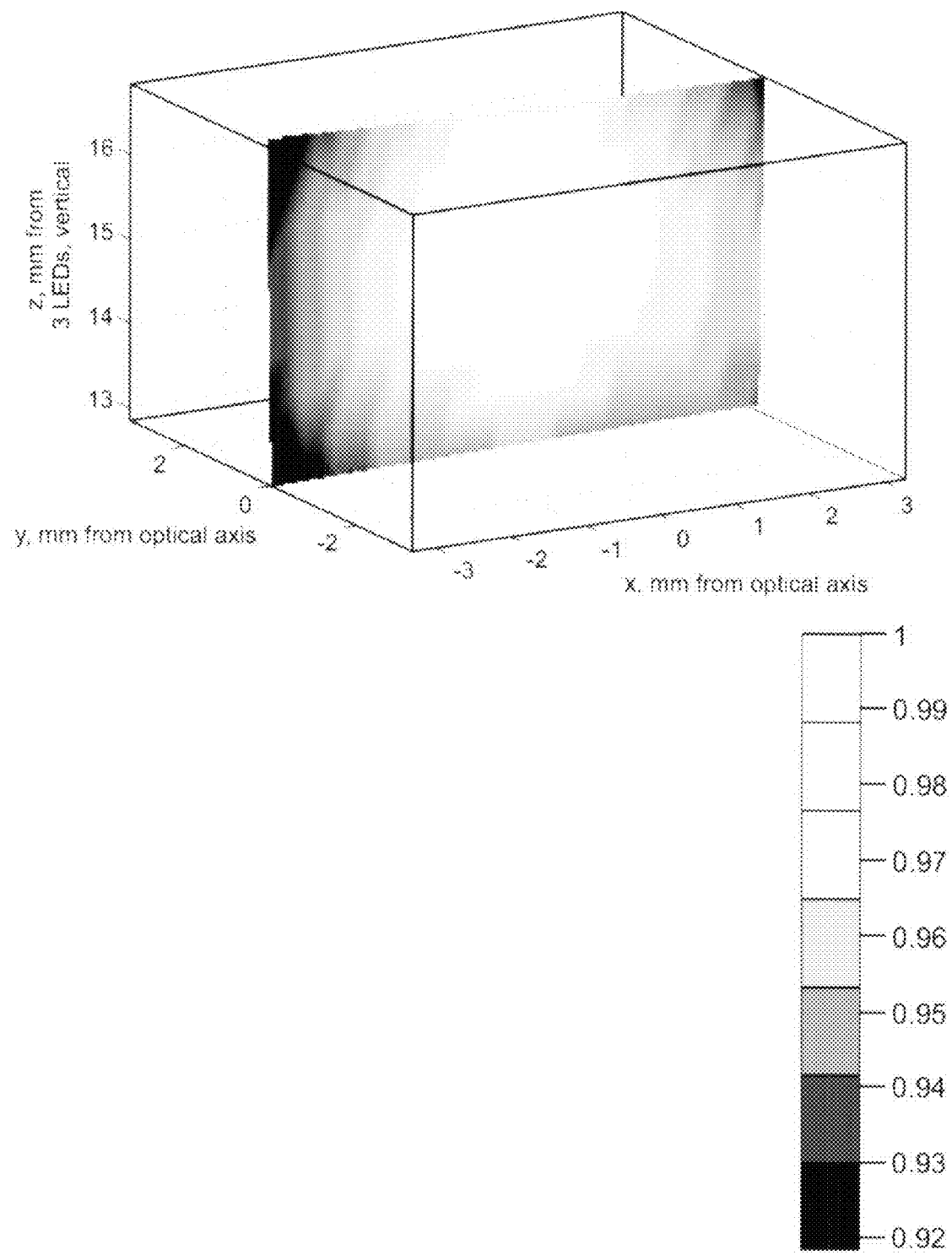
FIG. 3N is a photograph of filled contour schematic of the light irradiance available at (y,z) positions relative to the optical system of three equally spaced LEDs of the same wavelength and shown in its relative position with respect to the three dimensional graph of FIG. 3D. The scale indicates the percentage of light available at different positions, relative to the maximum irradiance within the volume depicted in FIG. 3D. The irradiance contour depicted by FIG. 3N is situated in a vertical (y,z) plane at a position of x=−0.1 mm from the system optical axis of the three equally spaced LEDs.

FIGS. 3E-3L show further irradiance contours taken as cross-sectional horizontal slices through the three-dimensional volume irradiance shown in FIG. 3D. Additionally, FIGS. 3M and 3N are irradiance contours taken as cross-sectional vertical slices in the (x,z) plane and the (y,z) plane, respectively, through the three-dimensional volume irradiance shown in FIG. 3D.

The contours shown in FIGS. 3C, 3E-3L and 3D are plotted for an illuminated object radius of less than 3.5 mm from the system optical axis situated at (x,y)=(0,0), in increments of 0.5 mm, and between 12.83 mm and 16.83 mm in the (x,y) plane above the plane in which the bases of the three LEDs reside. For purposes of generating the irradiance contours described herein, three LEDs having, for example, Osram part number LP E675-P1Q2-25, spaced equally about a radius of 16.08 mm, arranged co-planarly, emitting light having a wavelength of 562 nm (peak) and each having a viewing angle of 120 degrees, were used.

Figure 4:
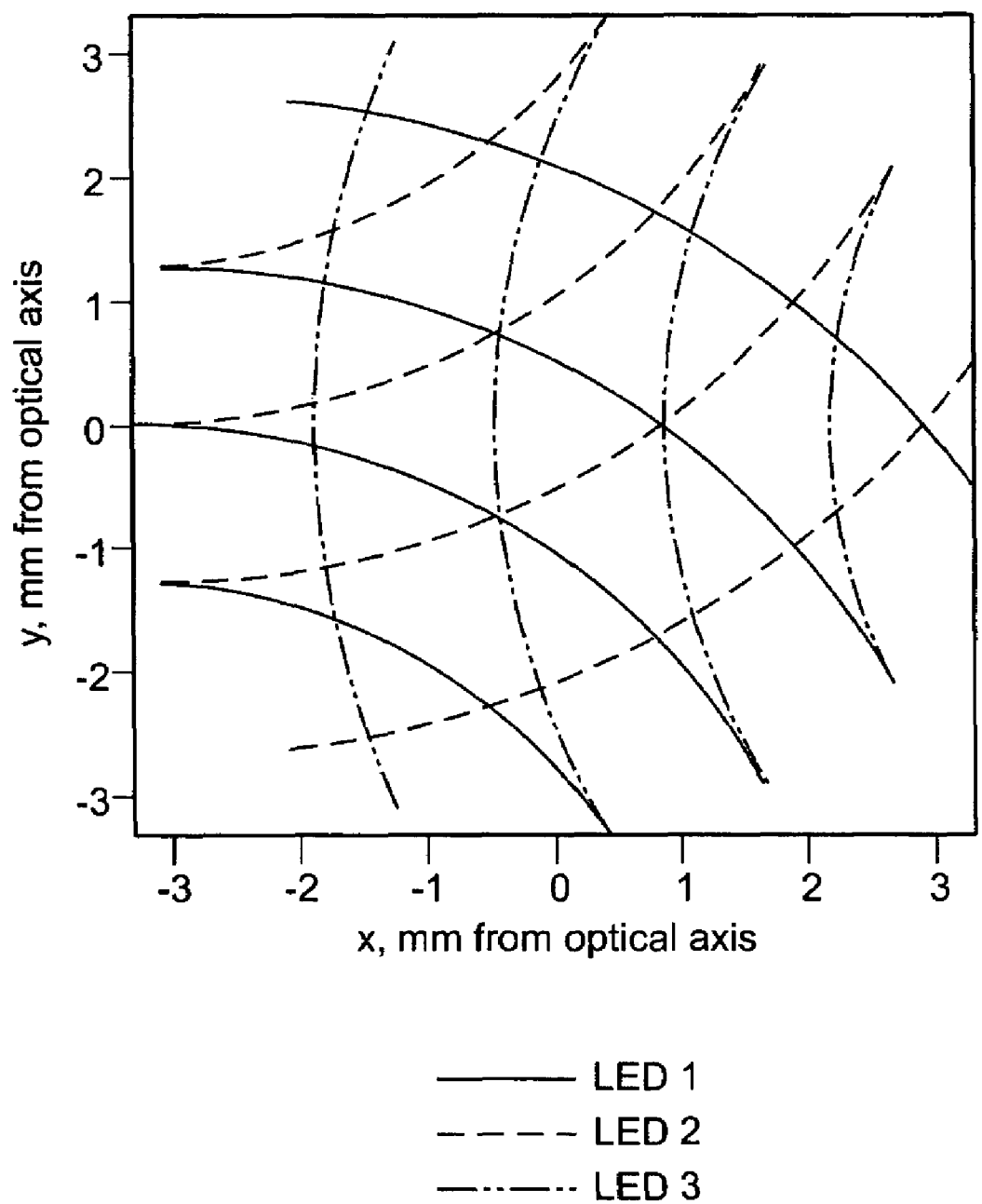
FIG. 4 is a top plan view of an illustration of overlapping contours of equal irradiance projected on a chemical reagent test slide and provided by the light source of the present invention, in the case of three symmetrically-located LEDs.

FIG. 4 illustrates irradiance contours on the chemical reagent test slide from each of three LEDs (i.e., LED1, LED2, and LED3) of the same wavelength spaced apart arcuately from each other by 120 degrees. The net irradiance from the three LEDs is shown in FIG. 3C. Again, by preferably positioning three LEDs 2 of the same wavelength 120 degrees apart from each other, illuminating them simultaneously and directing the light from each LED to the same plane, (x, y) plane and z-axis variability in the placement of the reagent test slide 6 is accommodated, as long as the film portion 10 resides within the volume 8 of substantially homogeneous light irradiance defined by the beams of overlapping light emitted simultaneously by the LEDs.

As mentioned previously, although the scope of the present invention encompasses at least two LEDs illuminated simultaneously, with their beams directed to the same plane, and preferably three or four LEDs illuminated simultaneously with their beams directed at the same plane, the present invention includes a plurality of LEDs, at least some of which emit light of different wavelengths, as the various test slides must be exposed to light of selected wavelengths in order to conduct different tests.

But if the object to be illuminated is rectangular, oval, or ellipse-shaped, and/or of greater width and depth than a dry chemistry slide, then many more LEDs may be needed to achieve substantially homogenous irradiance as reflected or fluoresced from the object. In these cases, a non-circular arrangement of these LEDs will often be preferable.

Figure 5:
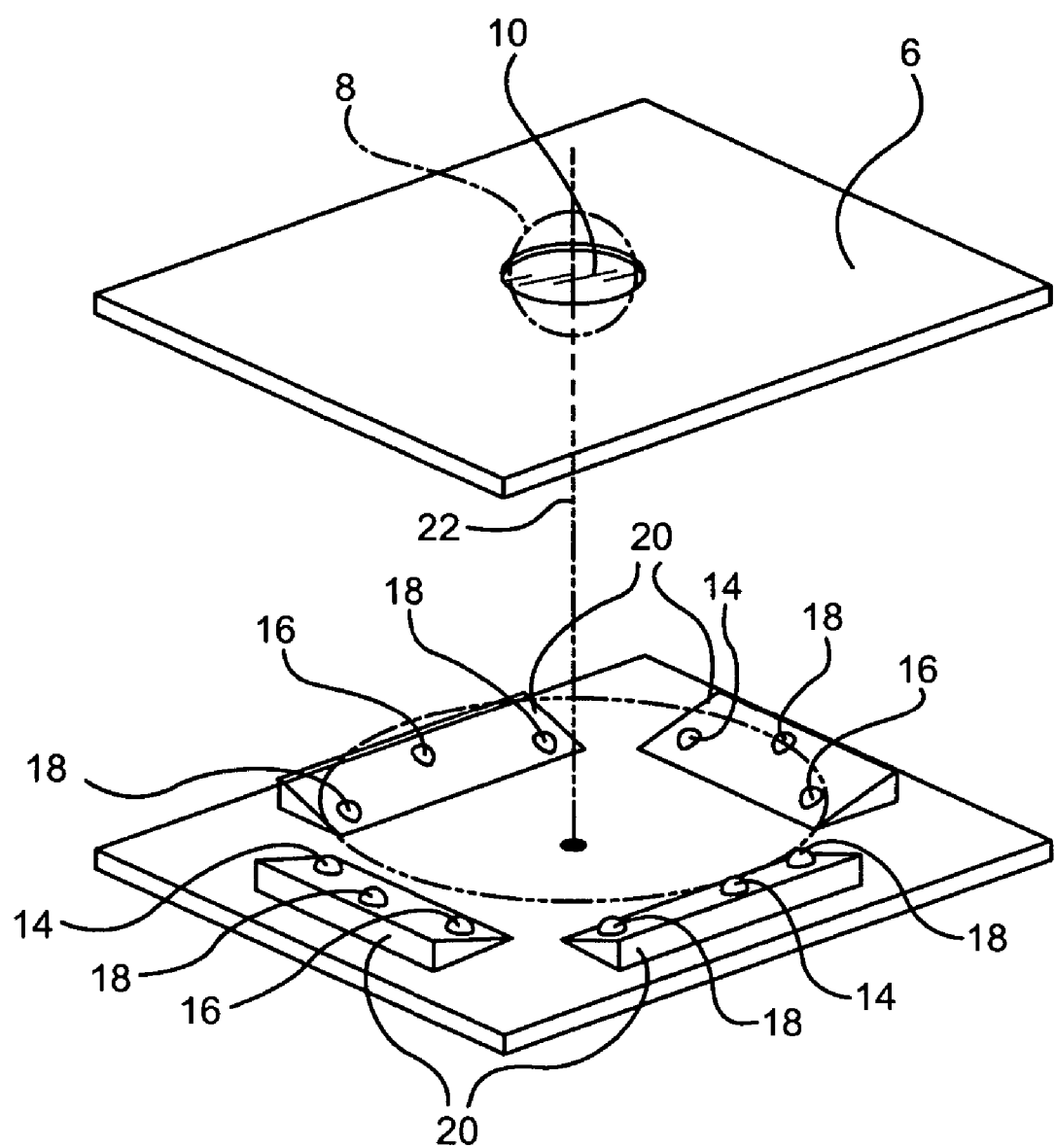
FIG. 5 is a top perspective view of one form of a support on which light emitting devices of the light source of the present invention are mounted.

More specifically, and as shown in FIG. 5, positioned radially about the system optical axis and spaced arcuately apart from one another are a plurality of red, blue and green LEDs 14, 16, 18. Preferably, there are three blue LEDs 16 which are spaced arcuately apart from one another by 120 degrees. There are also three red LEDs 14 which are similarly spaced apart arcuately from one another by 120 degrees.

It may happen that some LEDs, for example, green LEDs 18, are manufactured with a lower radiant flux than similarly manufactured LEDs of other wavelengths. Accordingly, if these lower intensity LEDs are used in the light source of the reflectometer of the present invention, then more of these LEDs than the higher intensity LEDs are used to illuminate the plane in which the reagent test slide resides. Accordingly, and as shown in FIG. 5, preferably six of the lower radiant flux (e.g., green) LEDs 18 are used, with adjacent of these LEDs being spaced apart arcuately from each other by 60 degrees. All LEDs 14-18 are positioned such that the light emitted from each is directed to a common plane, which corresponds to where the film portion 10 of the chemical reagent test slide 6 is situated.

The plurality of LEDs 14-18 is preferably mounted on a substrate provided for supporting the LEDs. The substrate may include one or more printed circuit boards 20, such as shown in the top perspective view of FIG. 5, where the LEDs are arranged radially about the system optical axis 22 of the LEDs 14-18, and with each LED of a given type (for example, green) spaced at approximately the same radius from the optical axis. The printed circuit boards 20 may reside in the same plane, with the LEDs 14-18 being mounted angularly on each board so that their light beams are directed toward a single plane. Preferably, the printed circuit boards 20 themselves may be angled such that a common plane illuminated by multiple LEDs situated on at least two circuit boards intersects a volume of substantially homogeneous illumination.

In practice, it will be easiest to select the LED mounting radius (perpendicular distance from the system optical axis 22), and vertical spacing and mounting angle (relative to the desired illumination plane) based in part on the emission profile of the LEDs selected. LEDs are commonly available in 120, 60, 30 and 15 degree "viewing angles," although other values are also commercially available. Typically, LED manufacturers specify the "viewing angle" as the angle of the circular sector within which the LED intensity is at least half that of the maximum emitted intensity. This sector will include the LED's axis of symmetry or the normal to its face. For an LED 2 with a smooth emission profile, such as depicted in FIG. 2, the maximum intensity often occurs normal to the LED's face or parallel to its axis of symmetry. For this invention, LEDs of wider viewing angles (e.g., 60-140 degrees) will be more effective toward forming an adequate volume of substantially homogeneous irradiance and are therefore preferred when the vertical spacing and LED mounting radius are on the order of 100 mm or less. In general, optimal LED viewing angle width and LED-to-illuminated object spacing are inversely related. Also, LEDs with smooth and consistent emission profiles are preferred for ease of placing them optimally relative to the desired volume of substantially homogeneous irradiance. However, neither wide viewing angles nor smooth nor highly consistent illumination is required to attain the improvements described in this invention to some degree, but optimization of these characteristics will help maximize the improvement of providing a more substantial and more consistent volume of homogeneous irradiance.

Figure 6A:
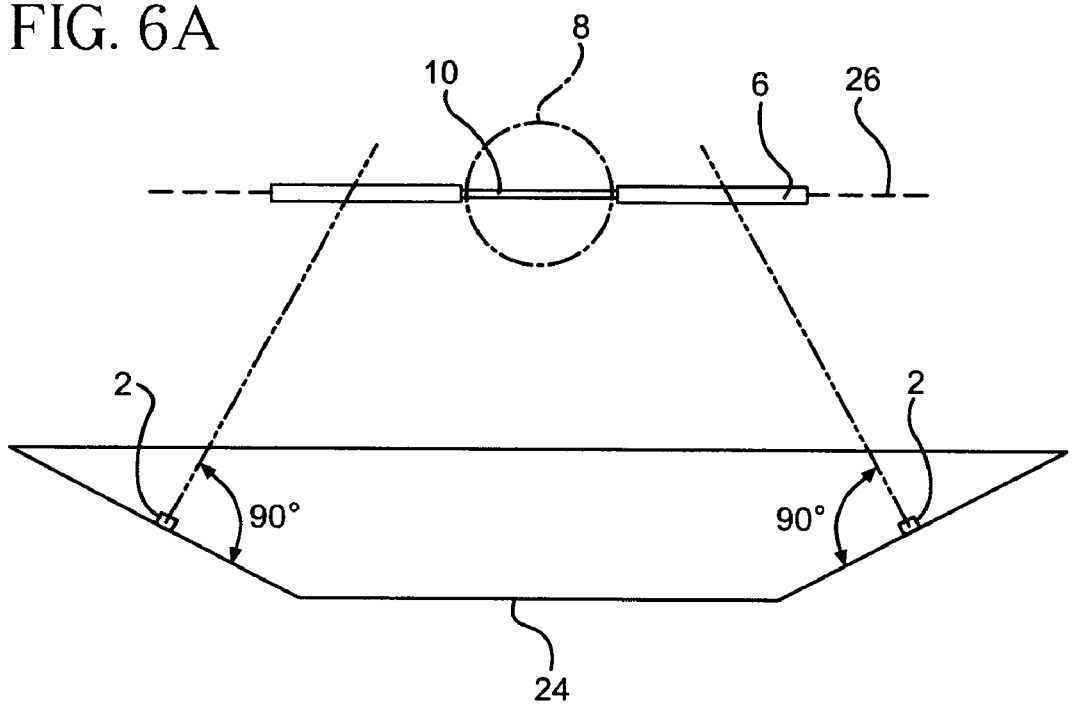
FIG. 6A is a side view of another form of a support for light emitting devices of the light source of the present invention.

Even more preferably, for irradiating a circular object, the substrate on which the LEDs are mounted may include a conically-shaped supporting structure 24, as shown in FIG. 6A. The surface on which the LEDs 2 are mounted is angled toward the illumination plane 26. The normal to the semiconductor die of each LED 2, which in most cases is along the axis of peak light intensity, is also shown in FIG. 6A.

Figure 6B:
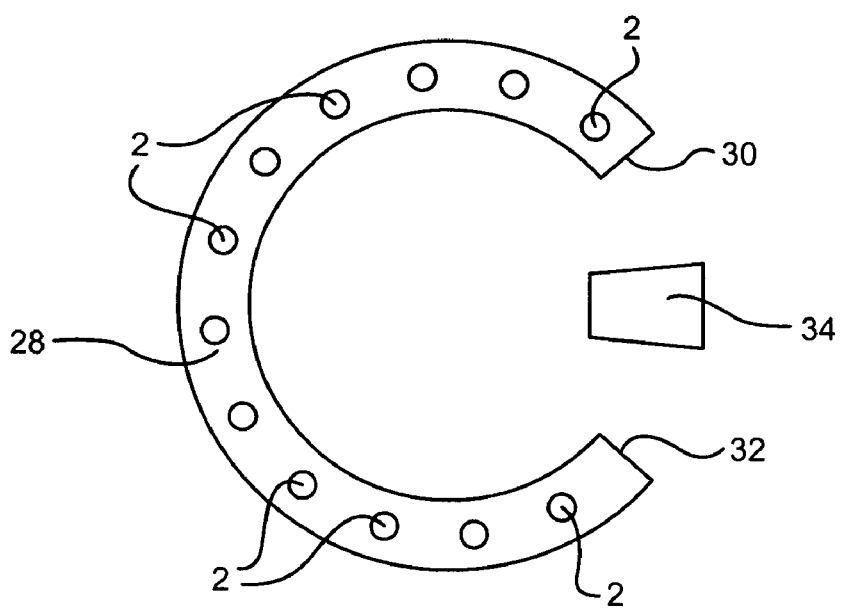
FIG. 6B is a top plan view of a support for mounting light emitting devices of the light source of the present invention.

One way of forming the conically-shaped supporting structure 24, in accordance with the present invention, is by using a planar C-shaped member 28 having a surface on which the LEDs 2 are mounted, as shown in FIG. 6B. The C-shaped member 28 has a first end 30 and a second end 32 circumferentially opposite the first end 30. The first end 30 and the second end 32 are brought together by a stable holding means 34, such as shown in FIG. 6B and described in greater detail below, defining the LED supporting structure with a truncated conical shape, i.e., the frustum of a right circular cone, such as shown in FIG. 6A. The C-shaped member 28 thus is preferably flexible, and may be, in one form of the present invention, a semi-rigid or flexible printed circuit board. Holding means, such as plate 34, and C-shaped member 28 are shown in FIG. 6B.

More specifically, the first and second ends 30, 32 of the C-shaped member 28 may be joined together by adhesive or a holding piece in the form of an elongated plate 34 that bridges the first and second ends of the C-shaped member 28 and preferably extends along the full length of the first and second ends 30, 32. The holding plate 34 is affixed to the first and second ends 30, 32 of the C-shaped member 28 by adhesive, hardware or the like, and has sufficient torsional rigidity that, when attached to the first and second ends of the C-shaped member, maintains the conical shape of the supporting structure especially at the juncture of the first and second ends 30, 32. Preferably, the C-shaped member is held in about its circumference by a fixture that is designed to force the member into a frustum shape, at the designed radius and angle. An example of such a holding means in shown in FIGS. 7A and 7B.

Figure 7A:
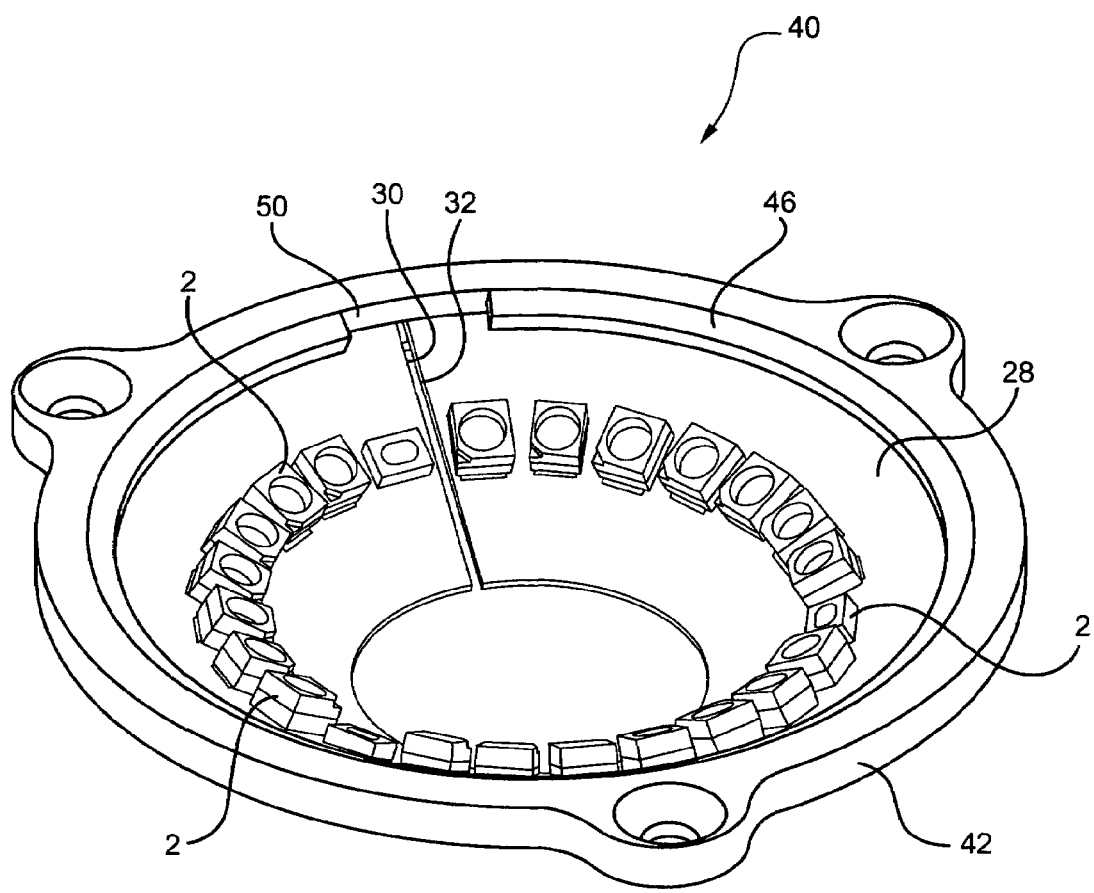
FIG. 7A is a perspective view of a fixture formed in accordance with the present invention for supporting the C-shaped printed circuit board shown in FIG. 6B in the shape of the frustum of a right circular cone.
Figure 7B:
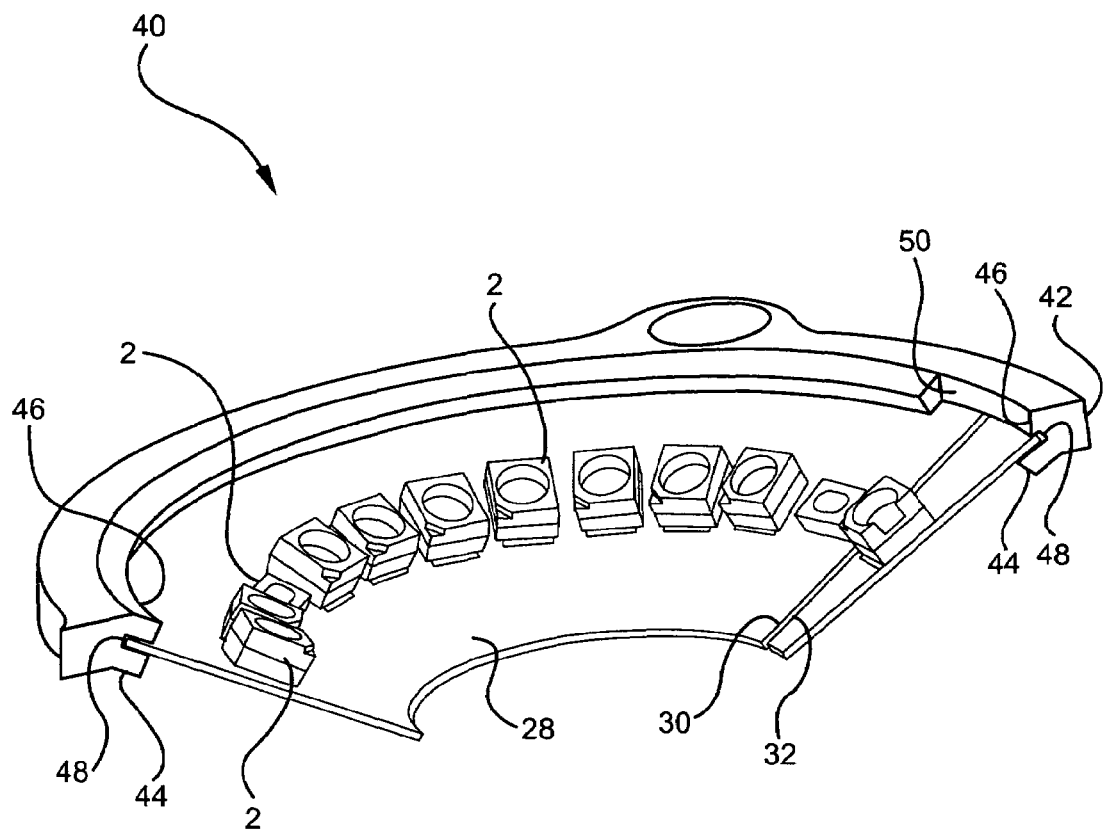
FIG. 7B is a perspective view of a cutaway portion of the mounting fixture of the present invention shown in FIG. 7A.

More specifically, and with reference to FIGS. 7A and 7B, a fixture 40 for supporting the C-shaped printed circuit board 28 on which are mounted a plurality of LEDs 2 or other light sources includes a circularly extending rim 42 having a radially inwardly extending lower shoulder 44 and a radially inwardly extending upper shoulder 46 situated in overlying relationship to the lower shoulder 44. The upper and lower shoulders 46, 44 are slightly spaced apart from one another to define a circular slot 48 therebetween, which is preferably angled downwardly from the radial plane in which the rim and shoulders reside, for at least partially receiving therein the outer radial edge portion of the printed circuit board 28. The upper shoulder 46 is preferably formed with a notch 50, or removed section, to facilitate the insertion of the printed circuit board outer edge portion into the receiving slot 48.

Preferably, the printed circuit board 28 is mounted to the fixture 40 by inserting the outer edge of the circuit board nearest one end portion 30 thereof into the fixture slot 48, starting at the notch 50 formed in the upper shoulder 46. The remainder of the outer edge of the circuit board 28 is then worked circularly from the end portion 30 into the slot 48 until the entire outer edge of the printed circuit board is properly seated in the slot, with the two end portions 30, 32 of the circuit board in proximity to or abutting each other, as shown in FIGS. 7A and 7B. The printed circuit board 28 is thus secured to the mounting fixture 40, and fixedly held in a frustum shape at a desired radius and angle. It should be noted here that the particular embodiment of the printed circuit board 28 of the present invention shown in FIGS. 7A and 7B includes twenty-four LEDs 2 or other miniature light sources (for examples, optical fiber outputs, or miniature lenses or apertures) mounted thereon for illuminating the test slide. However, the present invention should not be construed as being limited to a particular number of LEDs.

For illuminating a larger rectangular object, such as on the order of 40 mm wide and 15 mm deep, two angled circuit boards extending along and longer than the width of the object have been used. Both boards were placed in opposition, with LEDs thereon spaced along a 60 mm extent, and also with LED-to-LED spacing along this extent greater in the center than on either end. The boards were angled in such a way that a line perpendicular to the center of the front (contains the LEDs) face of either board would intersect the object plane farther on or past the center of the object, opposite the LED board. In this way (referring again to FIG. 2), increasingly more proximal portions of the object were illuminated at increasingly higher LED viewing angles, thereby forming the fundamental basis for balancing the irradiance on the object. In this case, there were either ten or twenty LEDs of a given type placed on each of the boards. The ten LEDs of one type were placed in a row along the long axis of the boards. The twenty LEDs of the other type were placed in two rows of ten each above and below the row of ten of the first type.

Important portions of an even larger rectangular object, on the order of 46 mm wide and 19 mm deep have also been homogeneously illuminated by two rows of boards containing four LEDs each. In this case, the LED boards extended parallel to the shorter axis of the object. The boards were placed closer together, effectively 8 mm from the horizontal center of the object, and each angled outward to homogeneously irradiate the object. The viewing angle of the LEDs used in this case was 60 degrees. A narrower viewing angle was more optimal because the LEDs were spaced farther (approximately 100 mm) from the object. A line perpendicular to the center of the face of either board would intersect the plane of the object well past its horizontal extent, to the left hand side of the object for the line coming from the left hand side board, and to the right hand side of the object for the line coming from the right hand side board. Accordingly, illumination of the object by LEDs on the left hand side board decreased across the width, going left to right, of the object. Similarly, illumination of the object by LEDs on the right hand side board increased across the width, again going left to right, of the object.

In all cases described above, the following method has been used to help decide the LED number, placement, and type (including viewing angle) selections.

Placements of LEDs

The position and angle of a single LED 2 relative to an object to be illuminated can be described simply, as in FIG. 2, when the goal is to minimize z-axis sensitivity of the irradiance provided by the LED source. But the arguments presented by FIG. 2 do not address x,y-plane irradiance homogeneity; to achieve this, more than one LED source is needed.

Two spaced-apart LEDs 2 can be configured relative to a surface and to one another so that the sum of their irradiances on the surface not only has minimal z-axis sensitivity, but better x,y-plane spatial homogeneity. Intuitively, maximum x,y plane irradiance homogeneity on the illuminated surface will occur when the LEDs are equally spaced from the normal to the center of the illuminated surface, along a line that is perpendicular to and intersects this normal. Similarly, optimal arrangement of three LEDs 2 will result in their being spaced at the corners of an equilateral triangle that is centered on and perpendicular to the surface normal. Four optimally-arranged LEDs will describe a square, etc. For illuminating a small circular area (such as approximately 10 mm in diameter or less) with wide viewing angle LEDs, or diffused narrow viewing angle LEDs, further increasing the LED number beyond four does little to improve the optimal x,y-plane irradiance homogeneity. Generally, more LEDs are needed to achieve optimal illumination as the area to be illuminated increases.

Estimating the optimal placements and angles of the LEDs 2 relative to the surface and to one another is not simple even when two LEDs are used. For placing a set of LEDs, relative to one another and to a surface to be illuminated, in such a way that the z-axis (vertical position of the surface relative to the LEDs) irradiance sensitivity and the x,y-plane (on the illuminated surface) irradiance homogeneity are optimized, a semi-automated numerical method was developed. This method is described below. It is general for illuminating diffusely-reflecting or fluorescing surfaces of a variety of shapes, as long as the object is substantially two-dimensional. This method does not address illumination of objects with features parallel to the optical axis that must be illuminated in a defined or optimized manner.

The method takes as inputs the following information:
1. The position, including angle, of one or more "boards" configured to hold LED or other point sources relative to the center of the object to be illuminated by the sources and detected by the imaging or reflected light detector.
2. The positions of one or more LED or other point sources on each "board."
3. The position of the detection system's entrance pupil, assumed parallel to the object, and with the centers of each coaxial.
4. The directional characteristics of the LED or other point source. This is the "viewing angle" function.
5. The intensity of the LED or other normal point source measured along its optical axis or the normal to its front face. Typically, all source intensities are set to one unit, but the algorithm also allows generation of a randomized, bell curve-shaped distribution of intensities, one for each LED, over a range that can be specified. The choice for all sources to have the same intensity is particularly useful for determining the optimal placements of the board(s) and the sources mounted on it or them.
6. The thickness and refractive index of an intervening window, if any. It is currently assumed that the window, if one is included, is parallel to both the object surface and entrance pupil, and that both surface-illuminating and detected surface-reflected light passes through the same window. Further desirable algorithm improvements include:
    a. Allowance for tilt of the window.
    b. Allowance for passage of light through the window only for one of illumination and detection.
    c. Allowance for two different windows, one for illumination and the other for detection.
7. The relative maximum intensity of specular vs. diffuse reflection, and the beam spread profile of the specularly reflected light. One can choose to not include specular reflections at all. A desirable algorithm improvement is to add compensation of the effects of an intervening window or windows, as in topic six (above).

Diffuse reflections are assumed to be Lambertian. However, following the method of Phong (Comm. ACM, 18/6 (June 1975), pp. 311-317), specular reflections are also modeled with some diffuse quality—as occur with object surfaces of chemistry slides and flow matrices, for example. The Phong model relates the detected specularly-reflected intensity to a viewing angle function, $I_s = \cos^n \eta$, where $\eta$ is the angle between the perfectly specular (angle of incidence=angle of reflection) reflected ray—here, called the "main" ray—and the chief ray from the object to the entrance pupil. The smaller the n value, the more diffuse quality is included in the specularly-reflected beam. Fluorescence, if it is being modeled instead of reflectance, is assumed to be isotropic.

In setting up the algorithm, one specifies the relative detected intensity of the most intense specular to the most intense diffuse rays. This value can be zero, which results in specular reflections not being included in the analysis—the desired case for systems (objects and optics) designed to detect the color or fluorescence change due to an indicator reaction. For most analyses run with this algorithm, the specular reflection contributions were set to zero. The selection of n is relevant when the specular reflection contributions cannot be ignored.

This method has been programmed as a combination of worksheet functions and Visual Basic for Applications code for use within Microsoft's Excel computer application. Essentially, this algorithm divides the object into a number of small, rectangular areas, and computes the contribution of that area to the detected (reflected or fluoresced) light, from illumination by each individual LED or other point source.

A simplified flow chart of the algorithm developed is described below.

First, compute items that do not need recalculation for each LED. The following values are preferably sequentially computed for each point (center of incremental rectangular area) on the object:

1. Chief ray from point angle of incidence, $\theta$
2. Refraction-corrected angle of incidence from point, $\theta'$
3. $\cos^{40}\theta'$ intensity falloff (ray from point), $f_r(\theta')$
4. Transmission of reflected ray from point, $T_r(\theta')$ Then, compute the items that do need recalculation for each LED. The "D" items pertain to the diffuse reflection or isotropic fluorescence calculation. As above, the following values are also preferably sequentially computed for each point (center of incremental rectangular area) on the object:

D.1 Source-to-point distance, i
D.2 Source emission angle (incident ray to source normal ray angle), $\delta$
D.3 Incident angle from source to point, $\zeta$
D.4 Refraction-corrected angle of incidence, $\zeta'$
D.5 Refraction-corrected source emission angle, $\delta'$ The following additional item is needed (recalculated for each LED and point) for the specular reflection calculation. The "S" designation is used to distinguish specular from diffuse. Refraction correction for the specular ray calculations is not included:

S.1 Specular main ray-to-chief ray angle, $\eta$

For detected light intensity I={(LED directionality)*(specular+diffuse reflection intensities)*(falloff)*(initial intensity)/(source-to-point distance)$^2$*(transmission losses)}, the following item is calculated:

I. Relative detected light intensity from source reflected by point, I

More details of the algorithm described above are set forth in Table I below, where the outline labels in this table correspond to the computational step labels (i.e., 1.-4., D.1-D.5, S.1, I) in the previous description of the simplified flow chart.

TABLE I

Object center is (x, y, z) = (0, 0, 0).
0. $s' = (x^2 + y^2 + h^2)^{1/2}$, where h = entrance pupil height from object center. Object and entrance pupil assumed parallel, and their centers coaxial.
1. $\theta = \tan^{-1}((x^2 + y^2)^{1/2}/h)$
2. $\theta'$ (refraction-corrected), determined numerically from $\theta$, height of entrance pupil above the object, and refractive index and thickness of window.
    2.a $\beta = \sin^{-1}(\sin(\theta')/r)$, where $r = n_w/n_a$, and $n_w$ and $n_a$ stand for the real refractive indices of the window and air, respectively.
3. $f_r(\theta') = \cos^4(\theta')$ intensity falloff; range = [0, 1].
4. $T_r(\theta') = \{\sin(2\theta') * \sin(2\beta)/\sin^2(\theta' + \beta)\}^2 * \{0.5 * [1 + 1/\cos^8(\theta' - \beta)]\}^{1/2}$ Note that this is for light passing through window, not just one surface; range = [0, 1].

The following calculations are for diffuse reflection or isotropic fluorescence:

D.1    $i = ((x - x')^2 + (y - y')^2 + z'^2)^{1/2}$, source-to-point distance, where the primed quantities refer to the LED positions.
    D.1.a $s = ((x - x_n')^2 + (y - y_n')^2)^{1/2}$, normal incidence-to-point distance, where the subscripted quantities refer to the object position of incidence of the LED normal ray.
    D.1.b $f = 0.5 * (i + s + p)$, half of sum of triangle perimeter, where p = the incident normal ray length.
D.2    $\delta = 2 * \cos^{-1}\{[f * (f - s)/(i * p)]^{1/2}\}$ (modification of Law of Cosines), incident point to source to source normal ray angle.
D.3    $\zeta = \cos^{-1}(z'/i)$, incident angle from source to point.
D.4    $\zeta'$ (refraction-corrected), determined numerically from $\zeta$, height of point source above the object, and refractive index and thickness of window.
    D.4.a $\gamma = \sin^{-1}(\sin(\zeta')/r)$, where $r = n_w/n_a$
D.5    $\delta' = \cos^{-1}\{\cos(\delta)\cos(\zeta' - \zeta) + \sin(\zeta' - \zeta)[\cos(\delta)\cos(\zeta) - \cos(\chi)]/\sin(\zeta)\}$ (refraction-corrected), where $\chi$ = the mounting angle of the source board.

The following calculations are for specular reflection:

S.0.a $p' = ((2x - x')^2 + (2y - y')^2 + (h - z')^2)^{1/2}$, reflected source (1:1 mirror image) to entrance pupil distance.
    S.0.b $g = 0.5 * (p' + i + s')$, half of sum of triangle perimeter.
S.1    $\eta = 2 * \cos^{-1}\{[g * (g - p')/(i * s')]^{1/2}\}$ (modification of Law of Cosines), specular ray to chief ray angle.

TABLE I-continued

The following calculations are for detected intensity:

I. $I = f_d(\delta') * [f_s(\eta) + f_d(\zeta')] * f_j(\theta') * I_0/i^2 * T_i(\zeta') * T_r(\theta')$, arbitrary intensity, but comparable point-to-point, and for illumination by different LEDs. Quantities not previously calculated or defined include:

$I_0$ —the intensity of the source normal to its face or on its optical axis.
   $f_d(\delta')$ —the "viewing angle" intensity function of the LED.
   $f_d(\zeta')$ —the diffuse (Lambertian) reflected or isotropic fluoresced intensity.
   $f_s(\eta)$ —the specular reflected intensity.
   $T_i(\zeta') = \{\sin(2\zeta') * \sin(2\gamma)/\sin^2(\zeta' + \gamma)\}^2 * \{0.5 * [1 + 1/\cos^8(\zeta' - \gamma)]\}^{1/2}$ Note that this is for light passing through window, not just one surface; range = [0, 1].
   Finally, note that the point-to-entrance pupil distance scaling is, in effect, included in $f_j(\theta')$ for cases where the z-axis distance is not varied. When it is varied, then the detected intensity I must be also multiplied by the square of the inverse of the distance from the center of the object to the entrance pupil. When the z-axis distance is to be varied, the entire calculation is performed for each z-axis distance, including recalculation of those items that do not need recalculation for each LED.

The algorithm is applied iteratively, where selected input parameters are varied over a programmed range and increment. A result of special interest for any set of input parameters is the sum of calculated reflectance intensities from all sources, for each point or incremental area of the object. A good layout of sources of a particular wavelength band, including their selections and placements, will have good x,y homogeneity—the standard deviation of the summed reflectances from all points within the region of interest on the object is low, or within specification. Furthermore, a good layout will also have low or within-specification z-axis sensitivity—each of the summed reflectances from all points within the region of interest on the object differs from the corresponding reflectances of the same points when the object is moved toward or away from the sources and entrance pupil (z-axis motion) by a specified distance.

Thus, placements and mounting angles of source-mounting boards, placements of the sources on the boards, and selection of the sources and the window, if any, can be guided by the desired detection properties, including high (x,y) field homogeneity and low z-axis sensitivity at the object's region of interest. For all results presented here, consideration of specular reflections was not included. These were shown to be minor (sensitivity approximately 1% or less relative to a white, Lambertian diffuse object) for the circular arrangement of LEDs illuminating a dry chemistry slide.

Other improvements, beyond those noted above, that could be effected include:

1. The capability to account for vignetting beyond simple $\cos^4\theta'$ falloff.
2. More automation of parameters variation, including iterative convergence on an optimum layout, guided by performance estimates for layouts tried.

Calibration Method

It is desirable to calibrate the LED or other source intensities in a way that is either non-iterative or rapidly converging, and fully automatic. A requirement for the calibration method disclosed here is that the source intensities must be individually adjustable, including an "off" setting. In this case, the calibration method is straightforward.

For the cases where the reflectance or fluorescence detector is a single photodiode, photomultiplier tube, or similar device, calibration is very simple. While illuminating a white reference slide or reference material located in the object plane, for example, the intensities of each LED of a given type are individually adjusted (with all other LEDs off) so that all detector readings are approximately identical for each LED, and also so that the detected intensity when all LEDs are turned on is a substantial portion of, but does not exceed, the dynamic range of the detector.

For example, the photocurrent from the detector is often converted to a voltage and amplified. If the dynamic range of this amplified output is [0, 5] V, then the drive currents of three LEDs of a given type might be individually adjusted to give an amplified output signal of 1.5 V for each case of only one LED turned on. Assuming negligibly small dark signal (all LEDs off) offsets when all three LEDs are turned on at their adjusted drive currents, the amplified output signal should be 4.5 V.

For cases where the detector is a digital camera, imaging array, machine vision system, or the like, calibration can be an extension of the source placement algorithm. In these cases, it will have been advantageous to select the incremental areas of the object (used for the LED placement algorithm) and the pixels of the detector for 1:1 spatial coincidence. While one pixel may correspond to one incremental area, it will be more common to group (and average the signals from) sets of adjacent pixels that spatially correspond with each incremental rectangular area of object.

Beginning with an optical layout developed and optimized to specifications for (x,y) illumination homogeneity and low z-axis sensitivity, as described previously, plus other parameters such as detected radiant intensity, source wavelength and bandwidth, etc., the preferred calibration method includes the steps of:

1. Placing a standard or reference material at the location of the object. This material should have reflection properties that are:

Substantially Lambertian.

Substantially homogeneous across an x,y region of interest.

Very similar to the slides, flow matrices, or other objects that are to be analyzed.

If front surface fluorescence is to be calibrated, the requirements are similar, but substitute "isotropic" for "Lambertian" and "fluorescence" for "reflection."

2. Turning on a single source, measuring the reflected intensity from each object area (where the object areas measured correspond to those defined in modeling the optical system, and may be the signal from a single pixel, the average of signals from a number of adjacent pixels, etc.), and comparing these values to the modeled intensities from the same areas, applying conversion factors and offsets as necessary.

A necessary conversion factor will transform the arbitrary intensity of the model to a signal, such as in volts, from the detector. If the pixel responses are linear and of substantially similar sensitivity, a single conversion factor and offset may be sufficient.

Non-linear detector responses, or substantially dissimilar sensitivities, or other optical factors may require use of added conversion constants. These may be determined empirically.

3. Adjusting the source's intensity and again measuring the reflected or fluoresced intensity from each physical area of the object repeatedly until the scaled intensities best match (such as by minimizing the root-mean-square of the measured minus modeled intensity residuals) the model's predicted reflected or fluoresced intensities for the coincident areas.

4. Turning off the source, and repeating Steps 2 and 3 for all sources.

5. Turning on all sources, their intensities set by the process described in the applications of Step 3, and verifying good x,y reflection homogeneity and detected intensity within a specified range.

This method has been demonstrated effective for calibration for both slide and flow matrix objects. But if Step 5 fails, and due to no apparatus malfunction, poor agreement between the model and the layout is strongly indicated. In particular, a potential reason for calibration failure can be that the "viewing angles" of the sources are not what was assumed in the modeling process.

Note that this calibration method does not require optimal placement of the LEDs or other point sources. Instead, the actual placement of the sources can be modeled, and the relative intensities of the sources, as modeled, can be adjusted to optimize desired optical parameters, such as x,y irradiance homogeneity or minimal z-axis sensitivity.

Performance compromises might be necessary for cases where the brightest source would be required to be much brighter than the dimmest, such as by a factor of four or more, in order to achieve optimal object irradiance. Cases like these could allow little leeway for the expected component-to-component variability of LED intensities if no performance compromises were made. A more robust design will allow for these intensity variations by carefully considering cases that would otherwise require the intensity of one LED of a given type to be more than four times greater than the intensity of another LED of the same type. In making such a selection, source control precision and accuracy must also be considered.

To effect calibration of the non-optimized source arrangement, the same steps described above for the optimized arrangement are followed. The greater the required intensity difference between the brightest and dimmest sources, the less source intensity adjustment will be possible.

Stated another way, the following description sets forth the steps of a method of calibrating the light sources of a reflectometer or a front surface fluorometer. The reflectometer or fluorometer has at least two light sources of the same wavelength, including a first light source and a second light source. It further has a reflectance or fluorescence detector associated with the at least two light sources. The at least two light sources illuminate a test object located in an object plane. Each of the at least two light sources has an individually adjustable light intensity. The method includes the steps of: placing a reference object in the object plane; energizing the first light source of the at least two light sources to emit light to illuminate the reference object located in the object plane, and simultaneously de-energizing all other light sources of the at least two light sources so as not to emit light therefrom; and detecting with the single detector light reflected or fluoresced by the reference object, the detector generating a first signal in response to the reflected or fluoresced light detected by the detector; measuring the first signal generated by the detector thereby to provide a measured first signal. The method further includes the steps of comparing the measured first signal with a first predetermined signal target value; adjusting the intensity of the first light source to be substantially equal to the first predetermined signal target value; energizing the second light source of the at least two light sources to emit light to illuminate the reference object located in the object plane, and simultaneously de-energizing all other light sources of the at least two light sources so as not to emit light therefrom; detecting with the detector light reflected or fluoresced by the reference object, the detector generating a second signal in response to the reflected or fluoresced light detected by the detector; and measuring the second signal generated by the detector thereby to provide a measured second signal.

The method further includes the steps of comparing the measured second signal with a second predetermined signal target value; and adjusting the intensity of the second light source to be substantially equal to the second predetermined signal target value.

Then, one by one, for all remaining sources, the method preferably includes the steps of: energizing the next available light source of the at least two light sources to emit light to illuminate the reference object located in the object plane, and simultaneously de-energizing all other light sources of the at least two light sources so as not to emit light therefrom; detecting with the detector light reflected or fluoresced by the reference object, the detector generating a signal in response to the reflected or fluoresced light detected by the detector; measuring the signal generated by the detector thereby to provide a measured signal; comparing the measured signal with a predetermined signal target value; and adjusting the intensity of the light source to be substantially equal to the predetermined signal target value.

Preferably, the first predetermined signal target value is substantially equal to the second predetermined signal target value, and the second predetermined signal target value is substantially equal to all other predetermined signal values for all remaining sources.

Preferably, the method of calibrating the light sources of a reflectometer or a front surface fluorometer further includes the steps of: energizing simultaneously the first light source, the second light source and all other light sources of the at least two light sources having the same wavelength to emit light to illuminate the reference object located in the object plane; detecting with the detector light reflected or fluoresced by the reference object, the detector generating a multiple source signal in response to the reflected or fluoresced light detected by the detector; measuring the multiple source signal generated by the detector thereby to provide a measured multiple source signal; and determining whether the measured multiple source signal is at least one of less than, equal to and greater than a predetermined multiple source signal target value.

Preferably, the reference object has light reflection properties that are substantially Lambertian and substantially homogeneous across the object plane.

In another preferred form of the present invention, a method of calibrating the light sources of a reflectometer or a front surface fluorometer will now be described. The reflectometer or fluorometer has at least two light sources of the same wavelength, including a first light source and a second light source, and further includes a detector having an array of light detecting pixels that coincide spatially with corresponding incremental areas of a test object located in an object plane. The array of light detecting pixels has one of at least two pixels including a first pixel and a second pixel and at least two groups of adjacent pixels including a first group of adjacent pixels and a second group of adjacent pixels. The at least two light sources illuminate the test object. Each of the at least two light sources has an individually adjustable light intensity. The preferred method includes the steps of: a) placing a reference object in the object plane; b) energizing the first light source of the at least two light sources of the same wavelength to emit light to illuminate the reference object located in the object plane, and simultaneously de-energizing all other light sources of the at least two light sources so as not to emit light therefrom; c) detecting with the detector light reflected or fluoresced by the reference object, the detector generating a first signal in response to the reflected or fluoresced light detected by the detector, the first signal corresponding to the reflected or fluoresced light detected by at least one of the first pixel of the array and the first group of adjacent pixels of the array; d) measuring the first signal generated by the detector thereby to provide a measured first signal for the first light source; and e) comparing the measured first signal for the first light source with a first predetermined signal target value for the first light source and generating a first comparative measurement for the first light source.

The method further includes the steps of: f) detecting with the detector light reflected or fluoresced by the reference object, the detector generating a second signal for the first light source in response to the reflected or fluoresced light detected by the detector, the second signal for the first light source corresponding to the reflected or fluoresced light detected by at least one of the second pixel of the array and the second group of adjacent pixels of the array; g) measuring the second signal for the first light source generated by the detector thereby to provide a measured second signal for the first light source; h) comparing the measured second signal for the first light source with a second predetermined signal target value for the first light source and generating a second comparative measurement for the first light source in response thereto; i) repeating steps f) through h) for at least one of all remaining pixels of the array and all remaining groups of adjacent pixels of the array, including measuring associated signals for the first light source generated by the detector and providing associated measured signals for the first light source, and comparing the associated measured signals for the first light source with respective predetermined signal target values for the first light source and generating respective comparative measurements for the first light source in response thereto; and j) adjusting the intensity of the first light source in response to the first comparative measurement for the first light source, the second comparative measurement for the first light source and all respective comparative measurements for the first light source to best collectively match the first predetermined signal target value for the first light source, the second predetermined signal target value for the first light source and all other respective predetermined signal target values for the first light source.

Furthermore, the method of the present invention includes the steps of: k) energizing the second light source of the at least two light sources to emit light to illuminate the reference object located in the object plane, and simultaneously de-energizing the all other light sources of the at least two light sources so as not to emit light therefrom; l) detecting with the detector light reflected or fluoresced by the reference object, the detector generating a first signal for the second light source in response to the reflected or fluoresced light detected by the detector, the first signal for the second light source corresponding to the reflected or fluoresced light detected by at least one of the first pixel of the array and the first group of adjacent pixels of the array; m) measuring the first signal for the second light source generated by the detector thereby to provide a measured first signal for the second light source; and n) comparing the measured first signal for the second light source with a first predetermined signal target value for the second light source and generating a first comparative measurement for the second light source.

Preferably, the method of the present invention includes the additional steps of: o) detecting with the detector light reflected or fluoresced by the reference object, the detector generating a second signal for the second light source in response to the reflected or fluoresced light detected by the detector, the second signal for the second light source corresponding to the reflected or fluoresced light detected by at least one of the second pixel of the array and the second group of adjacent pixels of the array; p) measuring the second signal for the second light source generated by the detector thereby to provide a measured second signal for the second light source; q) comparing the measured second signal for the second light source with a second predetermined signal target value for the second light source and generating a second comparative measurement for the second light source in response thereto; and r) repeating steps o) through q) for at least one of all remaining pixels of the array and all remaining groups of adjacent pixels of the array, including measuring associated signals for the second light source generated by the detector and providing associated measured signals for the second light source, and comparing the associated measured signals for the second light source with respective predetermined signal target values for the second light source and generating respective comparative measurements for the second light source in response thereto; s) adjusting the intensity of the second light source in response to the first comparative measurement for the second light source, the second comparative measurement for the second light source and all respective comparative measurements for the second light source to best collectively match the first predetermined signal target value for the second light source, the second predetermined signal target value for the second light source and all other respective predetermined signal target values for the second light source; and t) repeating steps k) through s) for all remaining light sources to be calibrated.

In a preferred form of the present invention, the method of calibrating the light sources of a reflectometer or a front surface fluorometer includes the further steps of: u) energizing simultaneously all of the light sources of the at least two light sources of the same wavelength to emit light to illuminate the reference object located in the object plane; v) detecting with the detector light reflected or fluoresced by the reference object, the detector generating a first multiple source signal in response to the reflected or fluoresced light detected by the detector, the first multiple source signal corresponding to the reflected or fluoresced light detected by the at least one of the first pixel of the array and the first group of adjacent pixels of the array; w) measuring the first multiple source signal generated by the detector thereby to provide a measured first multiple source signal; x) determining whether the measured first multiple source signal is at least one of less than, equal to and greater than the a first predetermined multiple source signal target value; y) detecting with the detector light reflected or fluoresced by the reference object, the detector generating a second multiple source signal in response to the reflected or fluoresced light detected by the detector, the second multiple source signal corresponding to the reflected or fluoresced light detected by the at least one of the second pixel of the array and the second group of adjacent pixels of the array; z) measuring the second multiple source signal generated by the detector thereby to provide a measured second multiple source signal; aa) determining whether the measured second multiple source signal is at least one of less than, equal to and greater than a predetermined second multiple source signal target value; and ab) repeating steps y) through aa) for at least one of all remaining pixels of the array and all remaining groups of adjacent pixels of the array, including measuring associated multiple source signals generated by the detector and providing associated measured multiple source signals, and determining whether the associated measured multiple source signals are at least one of less than, equal to and greater than respective predetermined multiple source signal target values. Preferably, the calibration method includes the additional step of determining the root-mean-squares of the differences between the measured multiple source signals and their respective predetermined multiple source signal target values in order to evaluate the effectiveness of the multiple source calibration.

Additionally, in accordance with another preferred form of the present invention, the method of calibrating the light sources of a reflectometer or front surface fluorometer, more specifically includes with the step j) of adjusting the intensity of the first light source in response to the first comparative measurement for the first light source, the second comparative measurement for the first light source and all respective comparative measurements for the first light source to best match the first predetermined signal target value for the first light source, the second predetermined signal target value for the first light source and all other respective predetermined signal target values for the first light source, the step of minimizing the root-mean-squares of the first comparative measurement for the first light source, the second comparative measurement for the first light source and all respective comparative measurements for the first light source, and includes with the step s) of adjusting the intensity of the second light source in response to the first comparative measurement for the second light source, the second comparative measurement for the second light source and all respective comparative measurements for the second light source to best collectively match the first predetermined signal target value for the second light source, the second predetermined signal target value for the second light source and all other respective predetermined signal target values for the second light source, the step of minimizing the root-mean-squares of the first comparative measurement for the second light source, the second comparative measurement for the second light source and all respective comparative measurements for the second light source, and repeating these steps of minimizing the root-mean-squares of all comparative measurements for each remaining light source energized individually and solely.

Multiple Wavelengths Illuminate One Object

In many cases, it will be advantageous to illuminate a slide or flow matrix sequentially, with more than one wavelength per slide or flow matrix. Some example cases include:

1. An interfering substance has a strong absorbance in the same wavelength region as the indicator chromophore. By using a second, different wavelength for the interferent, its contribution to the indicator wavelength's change of reflectance can be determined, allowing estimation of the change of reflectance due to the indicator alone, as if the interferent had not been present.
2. A weakly-absorbing or relatively analyte concentration-insensitive chromophore does not allow good detection signal-to-noise ratio. Using a second analysis wavelength may allow more accurate analyte concentration information.
3. A slide's or flow matrix's response includes two or more peaks that give different analyte information. A second or third, for example, detection wavelength may allow determining all of the desired analyte information without having to run the same type of slide or flow matrix two or more times.

Accordingly, it has been shown that the use of multiple LEDs, simultaneously illuminated and having the same wavelength, provides a substantially even distribution of light and a volume 8 of substantially homogenous irradiance, as shown in FIG. 3, which accounts for any z-axis variability, as well as variability in the (x,y) plane, arising from either positioning or development of the chemical reagent test slide 6 at the illumination plane 26 of the light source of the reflectometer. Thus, it is envisioned that more accurate optical readings will occur when the light source of the reflectometer of the present invention is used in a chemical analyzer to direct light on reagent test slides.

It is also envisioned to be within the scope of the present invention to change the intensity of one or more of the LEDs 2 of one wavelength relative to the other LEDs or LEDs of the same wavelength, in order to improve the consistency of the volume of substantially homogeneous irradiance provided by the simultaneous illumination of the LEDs. This may be accomplished by providing the capability for individually changing the drive current for each LED. The intensity of the LEDs 2 may also be made stronger or weaker by moving the substrate on which the LEDs are mounted closer to or farther from the reagent test slide 6 being illuminated. This would, of course, entail adjusting the geometry of the light source, as it is still desired to have the illumination plane 26 of optimum homogeneity coincide with the film portion 10 of the reagent test slide, of the binding area of a lateral flow matrix, etc., being tested.

The light source of the present invention also has applications in devices other than chemical analyzers, where a volume of substantially homogeneous irradiance is desired to counter the effects of (x, y) plane or z-axis variability in the positioning of an object to be illuminated. Such applications are envisioned to include use of the light source of the present invention for microscopes and densitometers.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A reflectometer for use with a chemical analyzer, which comprises:
    a plurality of light emitting diodes, at least some of which emit light of substantially the same wavelength and at least some of which emit light of a different wavelength than other light emitting diodes, the light emitting diodes of substantially the same wavelength being arcuately arranged about a circle having a predetermined radius, and being positioned to direct light emitted therefrom on a reagent test slide in proximity to an illumination plane, adjacent light emitting diodes being spaced apart from each other a predetermined distance, at least two of the light emitting diodes emitting light of substantially the same wavelength and being illuminatable simultaneously to provide a volume of substantially homogeneous irradiance at the illumination plane, each of the at least two of the light emitting diodes which emit light of substantially the same wavelength and are illuminatable simultaneously having a semiconductor die and exhibiting a non-peak intensity in emitted light which is less than the peak intensity at a non-peak light intensity axis extending from the die which is different from and peripheral to the peak light intensity axis, the at least two light emitting diodes being positioned to illuminate the reagent test slide at an angle to the peak light intensity axis of each of the at least two light emitting diodes, the peak light intensity axis of each of the at least two light emitting diodes not being directed at the reagent test slide, the peripheral, non-peak light intensity axis of each of the at least two light emitting diodes being directed at the reagent test slide to illuminate the reagent test slide; and an optical sensor, the optical sensor receiving light emitted by the plurality of light emitting diodes and reflected from a reagent test slide situated in proximity to the illumination plane and within the volume of substantially homogeneous irradiance.

2. A reflectometer for use with a chemical analyzer as defined by claim 1, which further comprises:
a substrate for supporting the plurality of light emitting diodes, the plurality of light emitting diodes being mounted on the substrate.

3. A reflectometer for use with a chemical analyzer as defined by claim 2, wherein the substrate includes at least one printed circuit board on which the plurality of light emitting diodes is mounted.

4. A reflectometer for use with a chemical analyzer as defined by claim 2, wherein the substrate includes a conically-shaped supporting structure having a surface on which the plurality of light emitting diodes is mounted, the surface being angled toward the illumination plane.

5. A reflectometer for use with a chemical analyzer as defined by claim 4, wherein the conically-shaped supporting surface is formed from a planar C-shaped member having a surface on which the plurality of light emitting diodes is mounted, the C-shaped member having a first end and a second end circumferentially opposite the first end, the first end and the second end being brought into close proximity to define the supporting structure with a generally conical shape.

6. A reflectometer for use with a chemical analyzer as defined by claim 1, wherein the plurality of light emitting diodes includes three light emitting diodes emitting substantially the same wavelength and spaced apart 120 degrees arcuately from each other, the three light emitting diodes being simultaneously illuminatable.

7. A reflectometer for use with a chemical analyzer as defined by claim 1, wherein the plurality of light emitting diodes includes at least two light emitting diodes emitting substantially the same wavelength and spaced apart arcuately from each other, the at least two light emitting diodes being simultaneously illuminatable.

8. A reflectometer for use with a chemical analyzer as defined by claim 1, wherein the plurality of light emitting diodes includes four light emitting diodes emitting substantially the same wavelength and spaced apart 90 degrees arcuately from each other, the four light emitting diodes being simultaneously illuminatable.

9. A reflectometer for use with a chemical analyzer as defined by claim 5, which further comprises
a circularly extending rim, the rim including a radially inwardly extending lower shoulder and a radially inwardly extending upper shoulder disposed in overlying relationship to the lower shoulder, the upper and lower shoulders defining between them a circular slot for at least partially receiving therein an outer radial edge portion of the C-shaped member.

10. A method of illuminating a reagent test slide in a chemical analyzer, which comprises the steps of:
causing at least two light emitting diodes of a plurality of light emitting diodes to emit light of substantially the same wavelength simultaneously, the light emitting diodes of the plurality of light emitting diodes being arcuately arranged about at least a partial circle having a predetermined radius, adjacent light emitting diodes of the plurality of light emitting diodes being spaced apart from each other, each of the at least two light emitting diodes having a semiconductor die and exhibiting a peak in emitted light intensity along a peak light intensity axis extending from the die and exhibiting a non-peak intensity in emitted light which is less than the peak intensity at a non-peak light intensity axis extending from the die which is different from and peripheral to the peak light intensity axis; and positioning the reagent test slide to be illuminated at an angle to the peak light intensity axis of each of the at least two light emitting diodes, wherein the angle is greater than zero degrees, the reagent test slide being situated in proximity to an illumination plane and being illuminated by the at least two light emitting diodes, the peak light intensity axis of each of the at least two light emitting diodes not being directed at the reagent test slide, the peripheral, non-peak light intensity axis of each of the at least two light emitting diodes being directed at the reagent test slide to illuminate the reagent test slide, the light simultaneously emitted by the at least two light emitting diodes on the reagent test slide in proximity to the illumination plane providing a volume of substantially homogeneous irradiance at the illumination plane.

11. A method of illuminating a reagent test slide in a chemical analyzer, which comprises the steps of:
causing at least one light emitting diode to emit light, the light emitting diode having a semiconductor die, the light emitting diode exhibiting a peak in emitted light intensity along a peak light intensity axis extending from the die and exhibiting a non-peak intensity in emitted light which is less than the peak intensity at a non-peak light intensity axis extending from the die which is different from and peripheral to the peak light intensity axis; and positioning the reagent test slide to be illuminated at an angle to the peak light intensity axis, wherein the angle is greater than zero degrees, the peak light intensity axis of the at least one light emitting diode not being directed at the reagent test slide, the peripheral, non-peak light intensity axis of the at least one light emitting diode being directed at the reagent test slide to illuminate the reagent test slide.

12. A method of illuminating a reagent test slide in a chemical analyzer as defined by claim 11,
wherein the light emitting diode exhibits an emission profile, and wherein the step of positioning the reagent test slide to be illuminated at an angle to the peak light intensity axis reduces the effects of small changes in position on the irradiance of the reagent test slide.

13. A reflectometer for use with a chemical analyzer as defined by claim 9, wherein the rim resides in a radial plane, and wherein the circular slot is angled at a predetermined angle with respect to the radial plane in which the rim resides, the angle being greater than zero, thereby holding the C-shaped member in the shape of a frustum of a right circular cone.

14. In combination:
  a light source for a reflectometer for use with a chemical analyzer, the light source comprising:
  a plurality of light emitting devices, the light emitting devices being arcuately arranged about at least a partial circle having a predetermined radius, and being positioned to direct light emitted therefrom on an illumination plane, adjacent light emitting devices being spaced from each other a predetermined distance, at least two of the light emitting devices emitting light of the same wavelength and being illuminated simultaneously to provide a volume of substantially homogeneous irradiance at the illumination plane; and
  a substrate for supporting the plurality of light emitting devices, the plurality of light emitting devices being mounted on the substrate, wherein the substrate includes at least one printed circuit board on which the plurality of light emitting devices is mounted, and wherein the conically-shaped supporting surface is formed from a planar C-shaped member having a surface on which the plurality of light emitting devices is mounted, the C-shaped member having a first end and a second end circumferentially opposite the first end, the first end and the second end being brought into close proximity to define the supporting structure with a generally conical shape; and
  a fixture cooperating with the light source, the fixture comprising:
  a circularly extending rim, the rim including a radially inwardly extending lower shoulder and a radially inwardly extending upper shoulder disposed in overlying relationship to the lower shoulder, the upper and lower shoulders defining between them a circular slot for at least partially receiving therein an outer radial edge portion of the C-shaped member, wherein the rim resides in a radial plane, and wherein the circular slot is angled at a predetermined angle with respect to the radial plane in which the rim resides, the angle being greater than zero, thereby holding the C-shaped member in the shape of a frustum of a right circular cone, and wherein a notch is formed in the upper shoulder of the rim to facilitate insertion of the C-shaped member into the rim slot.

* * * * *